(12) United States Patent
Bethge

(10) Patent No.: US 11,459,352 B2
(45) Date of Patent: Oct. 4, 2022

(54) METHOD FOR POLYALKOXYLATION OF NUCLEIC ACIDS THAT ENABLES RECOVERY AND REUSE OF EXCESS POLYALKOXYLATION REAGENT

(71) Applicant: NOXXON Pharma AG, Berlin (DE)

(72) Inventor: Lucas Bethge, Potsdam (DE)

(73) Assignee: NOXXON Pharma AG, Berlin (DE)

( * ) Notice: Subject to any disclaimer, the term of this patent is extended or adjusted under 35 U.S.C. 154(b) by 271 days.

(21) Appl. No.: 16/464,291

(22) PCT Filed: Nov. 30, 2017

(86) PCT No.: PCT/EP2017/001399
§ 371 (c)(1),
(2) Date: May 27, 2019

(87) PCT Pub. No.: WO2018/099600
PCT Pub. Date: Jun. 7, 2018

(65) Prior Publication Data
US 2020/0291057 A1  Sep. 17, 2020

(30) Foreign Application Priority Data
Nov. 30, 2016 (EP) ..................................... 16201391

(51) Int. Cl.
| C07H 21/02 | (2006.01) |
| C07H 21/04 | (2006.01) |
| C07H 21/00 | (2006.01) |
| C12N 15/113 | (2010.01) |

(52) U.S. Cl.
CPC ........... *C07H 21/00* (2013.01); *C12N 15/113* (2013.01)

(58) Field of Classification Search
CPC ........................... C12N 15/113; C12N 2310/16
See application file for complete search history.

(56) References Cited

U.S. PATENT DOCUMENTS

| 8,207,298 B2 | 6/2012 | Hatala |
| 8,841,431 B2 | 9/2014 | Sell et al. |
| 8,877,709 B2 | 11/2014 | Schechter et al. |
| 9,878,044 B2 * | 1/2018 | Platscher ................. C07K 5/02 |
| 2004/0180412 A1 | 9/2004 | Liu et al. |
| 2009/0192100 A1 * | 7/2009 | Vater ....................... A61P 35/04 514/44 R |
| 2009/0286955 A1 | 11/2009 | Hatala |
| 2012/0277419 A1 | 1/2012 | Brooks |
| 2015/0232852 A1 | 8/2015 | Purschke et al. |
| 2017/0166604 A1 | 6/2017 | Bethge |

FOREIGN PATENT DOCUMENTS

WO   WO 2012/149198 A2 * 11/2012   ........... C12N 15/113

OTHER PUBLICATIONS

Bayryamov (HAYHHM TPYAOBE, 49, 9.1, 2010, 41-48).*
Chan & White, eds., "Fmoc . . . Synthesis," Oxford Univ Press, 2000, p. 41-76.
Bonora et al., "Polyethylene . . . oligonucleotides," App Biochem Biotech Part A Enz Eng 54(1-3)3-17, 1995.
Bonora, "Polymer . . . oligonucleotides," J Bioactive Comp Poly 17(5)377-378, 2002.
Hoffman et al., "RNA . . . conjugation," Curr Protocols NA Chem p. 4.46.1-4.46.30, John Wiley, NJ, 2011.

* cited by examiner

Primary Examiner — Amy H Bowman
(74) Attorney, Agent, or Firm — MDIP LLC

(57) ABSTRACT

The present invention is related to a method for the preparation of a modified nucleic acid molecule comprising a nucleic acid moiety and a non-nucleic acid moiety by reacting a first reactant and a second reactant, wherein the first reactant comprises the non-nucleic acid moiety and a carboxyl group, and wherein the second reactant is an amino-modified nucleic acid molecule comprising the nucleic acid moiety and an amino modification comprising an amino group which is attached to the nucleic acid moiety, wherein the method comprises the following steps: a) activating the first reactant, preferably the carboxyl group of the first reactant, by a condensation reagent in a water miscible organic solvent, and b) reacting the activated first reactant, preferably the activated carboxyl group of the first reactant, of step a) and the second reactant, preferably the amino group of the amino modification of the amino-modified nucleic acid molecule which has been dissolved in water or a mixture of a water miscible organic solvent and water, whereby the modified nucleic acid molecule is formed.

23 Claims, 9 Drawing Sheets
Specification includes a Sequence Listing.

building blocks for 5'-amino-modifications building blocks for internal amino-modifications building blocks for 3'-amino-modifications

A)

B)

C)
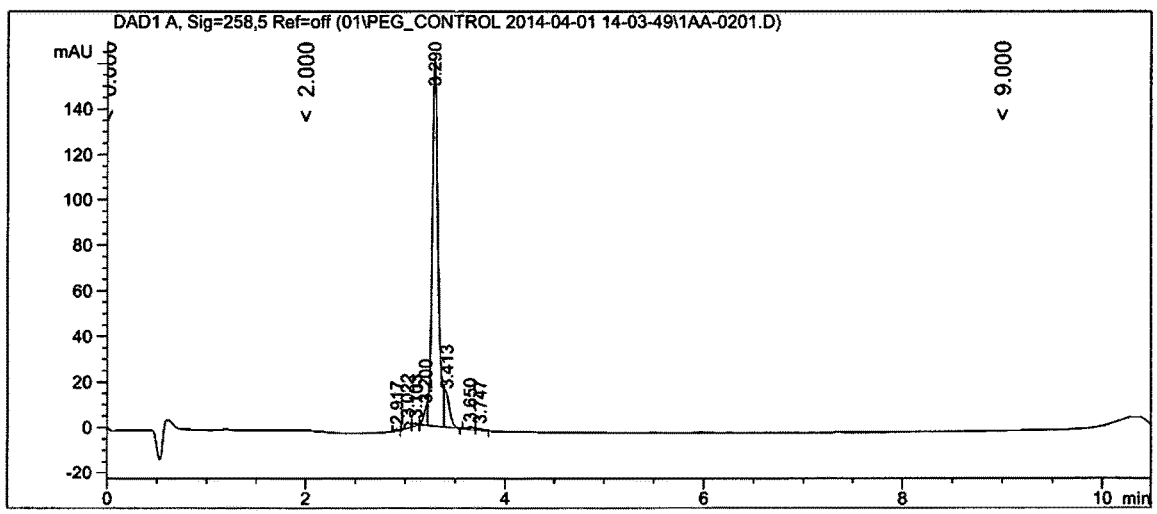
D)
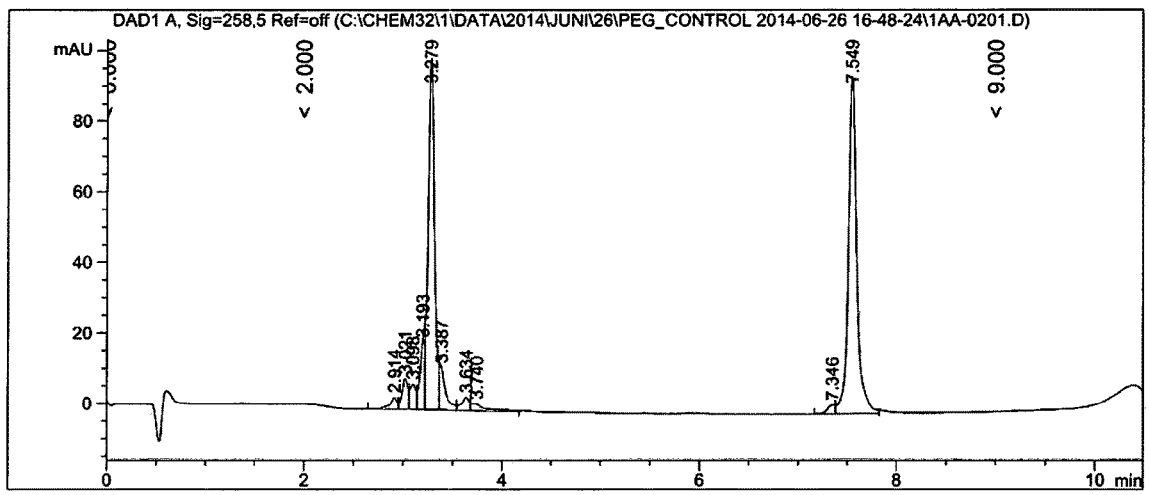
Figure 3 (continuation)

A)

B)

c)
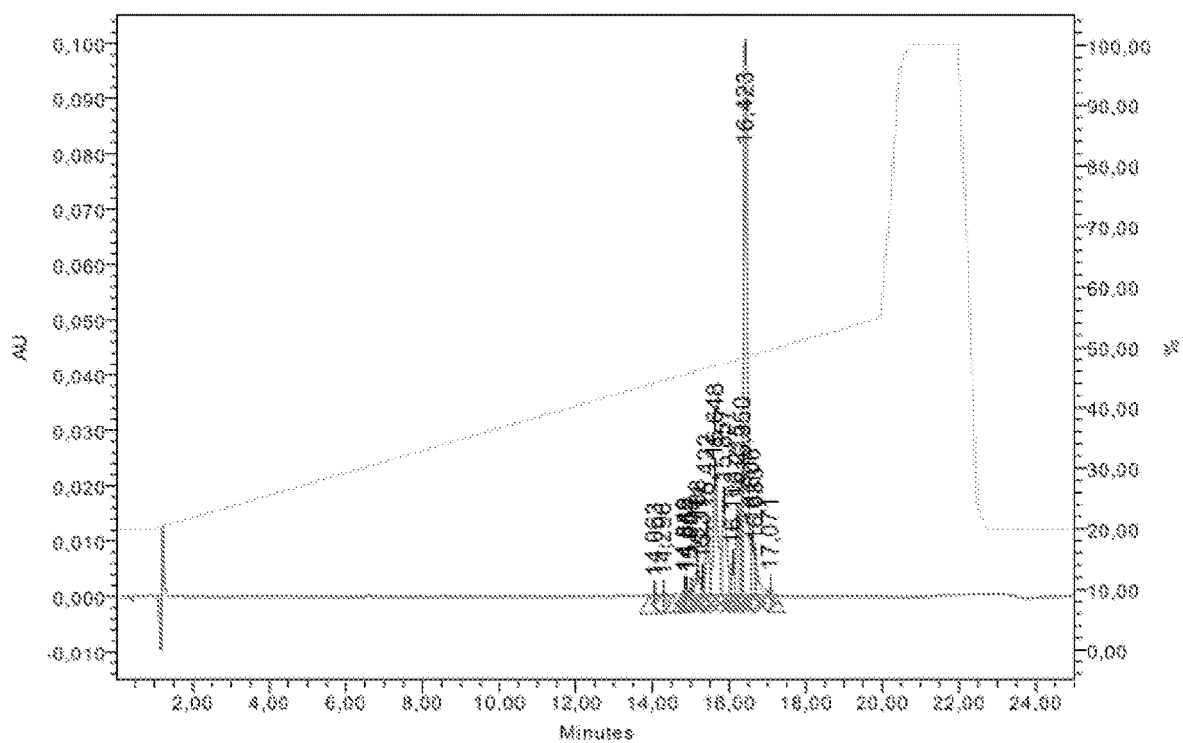
Figure 4 (continuation)

A)

B)

C)
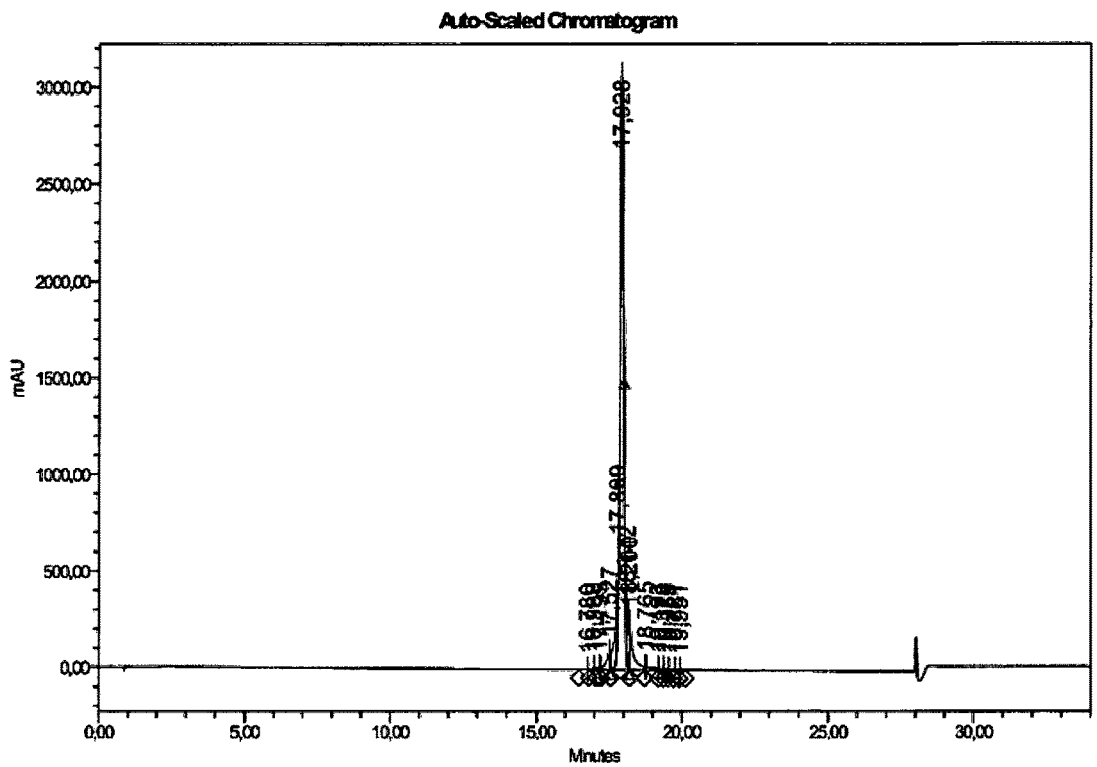
D)
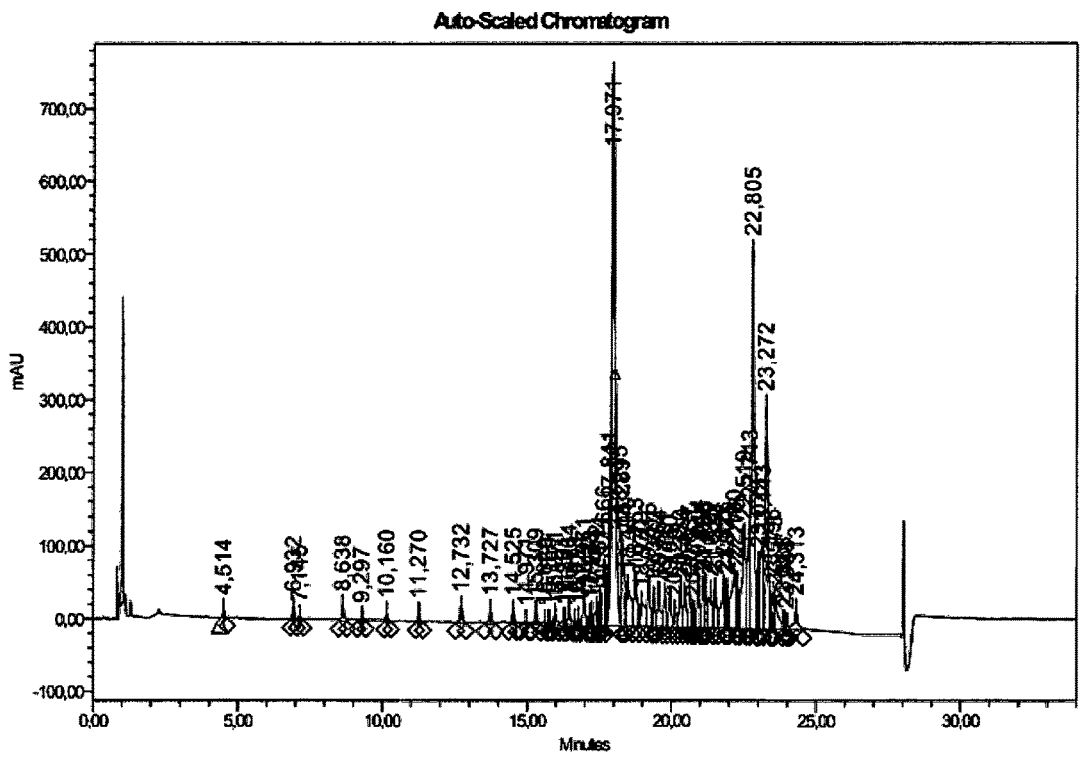
Figure 5 (continuation)

E)
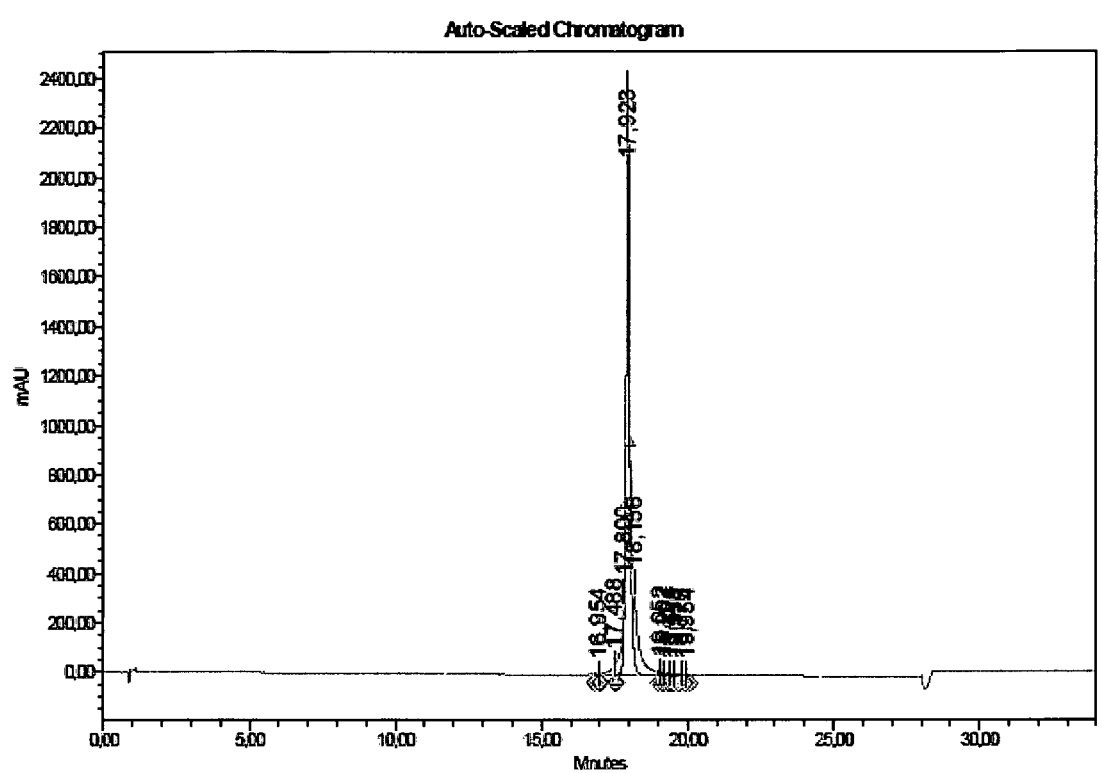
Figure 5 (continuation)

METHOD FOR POLYALKOXYLATION OF NUCLEIC ACIDS THAT ENABLES RECOVERY AND REUSE OF EXCESS POLYALKOXYLATION REAGENT

The present invention is related to a method for the preparation of a modified nucleic acid molecule comprising a nucleic acid moiety and a non-nucleic acid moiety by reacting a first reactant and a second reactant, wherein the first reactant comprises the non-nucleic acid moiety and a carboxyl group and wherein the second reactant is an amino-modified nucleic acid molecule comprising the nucleic acid moiety and an amino modification comprising an amino group attached to the nucleic acid moiety, a modified nucleic acid molecule obtained by the method, a modified nucleic acid molecule obtained by the method for use in therapy, a modified nucleic acid molecule obtained by the method for use in diagnosis, and use of a modified nucleic acid molecule obtained by the method in an in vitro method for analyzing a sample.

Conjuagation of drugs, such as nucleic acids, peptides, proteins and nanoparticles to other moieties such as polyalkoxy compounds, is widely used to increase the bioavailability, stability, safety, and efficacy for therapeutic applications. Within the field of oligonucleotide therapeutics, aptamers and spiegelmers (also referred to as mirror-imaged aptamers) are commonly polyalkoxylated. Polyethylene glycol (abbr. PEG) is a commonly used polyalkoxy compound that has been approved by the Food and Drug Administration as part of drugs administered intravenously, orally and dermally.

In general, a polyalkoxylated nucleic acid is prepared by a method that first assembles the nucleic acid containing a reactive group on a solid-phase (Hoffmann et. al, *Current Protocols in Nucleic Acid Chemistry* 2011, 4:4.46.1-4.46.30). After cleavage from solid-phase and deprotection the synthesized nucleic acid is purified by methods such as Reversed Phase High Performance Liquid Chromatography (abbr. RP-HPLC) or Ion Exchange Chromatography High Performance Liquid Chromatography (abbr. IEX-HPLC) or ultrafiltration (abbr. UF). The reactive group of the nucleic acid can then be reacted with a polyalkoxy compound having a suitable matching reactive group to form a conjugate of the polyalkoxy compound and the nucleic acid. After conjugation, the crude product consisting of polyalkoxylated nucleic acid molecules and non-polyalkoxylated nucleic acid molecules is purified by methods that can be a combination of HPLC, in particular RP- or IEX-HPLC, and ultrafiltration.

The yield of a polyalkoxylation reaction depends on the nature and purity of the nucleic acid to be polyalkoxylated, the type of the polyalkoxylation reaction and on the reaction condition itself. The most commonly used reaction types used for the polyalkoxylation of nucleic acids are:

a) aminolysis of polyalkoxycarboxylic acid active ester by an amino-modified oligonucleotide in presence of a base;

b) addition of a thiol-modified oligonucleotide to a polyalkoxy compound bearing a maleimide group; and c) 1,3-dipolar cycloaddition of an azide-modified oligonucleotide with a polyalkoxy compound bearing an alkyne group or of an alkyne-modified oligonucleotide with a polyalkoxy compound bearing an azide group.

The most widely used polyalkoxylation reaction is aminolysis of a polyalkoxycarboxylic acid active ester by an amino-modified oligonucleotide in the presence of a base. The reaction is fast and easily scalable. Maleimide-thiol addition does not require any base and is a fast and selective reaction, but the thiol needs to be set free from the disulfide precursor in a separate reaction step with a reducing agent such as DTT. Excess DTT must be removed completely before the conjugation reaction as it will also undergo addition to the maleimide and will therefore reduce the yield. Removal of DTT must be fast as the released thiol will undergo oxidation. This complicates the use for large scale production. 1,3-dipolar cycloaddition, also referred to as "click-reaction", either needs the presence of copper as a catalyst or a sterically constrained alkyne species. For the metal-free "click-reaction" either the azide or the sterically constrained alkyne needs to be introduced to the oligonucleotide post synthetically as both are sensitive towards nucleophilic bases such as methylamine/ammonia used for cleavage and deprotection of oligonucleotides.

Taking the limitations of maleimide-thiol addition and "click-reaction" into account, formation of polyalkoxlated oligonucleotides at large scale is best performed by aminolysis of a polyalkoxycarboxylic acid active ester by an amino-modified oligonucleotide. Typically, polyalkoxycarboxylic acids are activated as N-hydroxy succinimide esters which are prepared in a separate reaction, purified and stored until usage. Due to their reactive nature, the aforementioned esters are prone to hydrolysis to the corresponding free polyalkoxycarboxylic acid and N-hydroxy succinimide. This inevitably calls for precautions during handling, storing or shipping of such substances.

The problem underlying the present invention is the provision of a method for the preparation of a modified nucleic acid molecule and more specifically a polyalkoxylated nucleic acid molecule such as a PEGylated nucleic acid molecule.

This and other problems are solved by the subject matter of the attached independent claims. Preferred embodiments may be taken from the attached dependent claims.

The problem underlying the present invention is more specifically solved in a first aspect which is also a first embodiment of the first aspect, by a method for the preparation of a modified nucleic acid molecule comprising a nucleic acid moiety and a non-nucleic acid moiety by reacting a first reactant and a second reactant, wherein the first reactant comprises the non-nucleic acid moiety and a carboxyl group, and wherein the second reactant is an amino-modified nucleic acid molecule comprising the nucleic acid moiety and an amino modification comprising an amino group which is attached to the nucleic acid moiety, wherein the method comprises the following steps:

a) activating the first reactant, preferably the carboxyl group of the first reactant, by a condensation reagent in a water miscible organic solvent, and b) reacting the activated first reactant, preferably the activated carboxyl group of the first reactant, of step a) and the second reactant, preferably the amino group of the amino modification of the amino-modified nucleic acid molecule which has been dissolved in water or a mixture of a water miscible organic solvent and water, whereby the modified nucleic acid molecule is formed.

In a second embodiment of the first aspect which is also an embodiment of the first embodiment of the first aspect, the amino-modified nucleic acid molecule is dissolved in a mixture of water and a water miscible organic solvent in the presence of a quaternary ammonium salt.

In a third embodiment of the first aspect which is also an embodiment of the first and second embodiment of the first aspect, the activated first reactant of step a) is added to the amino-modified nucleic acid molecule dissolved in water or in a mixture of a water miscible organic solvent and water.

In a fourth embodiment of the first aspect which is also an embodiment of the first, second and third embodiment of the first aspect, the first reactant and/or the non-nucleic acid moiety is selected from the group comprising a polyalkoxy compound, a peptide, a protein, a glycoprotein, a nucleic acid, a carbohydrate moiety and a chemical moiety different from a peptide, a protein, a glycoprotein, a nucleic acid and/or a carbohydrate-based moiety, preferably the first reactant and/or the non-nucleic acid moiety is a polyalkoxy compound.

In a fifth embodiment of the first aspect which is also an embodiment of the first, second, third and fourth embodiment of the first aspect, the amino-modified nucleic acid molecule is suitable for use in an analytical method, in diagnosis and/or therapy.

In a sixth embodiment of the first aspect which is also an embodiment of the first, second, third, fourth and fifth embodiment of the first aspect, the amino-modified nucleic acid molecule is selected from the group comprising amino-modified aptamers, amino-modified Spiegelmers, amino-modified immunostimulatory nucleic acids, amino-modified siRNA, amino-modified miRNA molecules and amino-modified nucleic acid antisense molecules, preferably aptamers are aptamers consisting of L- and/or D-nucleotides and/or wherein the nucleic acid moiety is selected from the group comprising aptamers, Spiegelmers, immunostimulatory nucleic acids, siRNA, miRNA molecules and nucleic acid antisense molecules, preferably aptamers are aptamers consisting of L- and/or D-nucleotides.

In a seventh embodiment of the first aspect which is also an embodiment of the first, second, third, fourth, fifth and sixth embodiment of the first aspect, in step b) an excess of molecules of the activated first reactant over the amino-modified nucleic acid molecules is used.

In an eighth embodiment of the first aspect which is also an embodiment of the seventh embodiment of the first aspect, the excess is expressed as a molar ratio of molecules of the activated first reactant and the amino-modified nucleic acid molecules, wherein the molar ratio is from about 1.1 to about 10, preferably from about 1.5 to about 3.5.

In a ninth embodiment of the first aspect which is also an embodiment of the first, second, third, fourth, fifth, sixth, seventh and eighth embodiment of the first aspect, for activating the first reactant according to step a) the first reactant is dissolved in a water miscible organic solvent, and a condensing agent and a base, preferably first a condensing agent and subsequently a base, are added, wherein preferably the condensing agent is dissolved in a water miscible organic solvent.

In a tenth embodiment of the first aspect which is also an embodiment of the ninth embodiment of the first aspect, the base is a non-nucleophilic base.

In an eleventh embodiment of the first aspect which is also an embodiment of the ninth and tenth embodiment of the first aspect, between 0.25 min to 60 min, preferably between 0.5 min to 20 min and more preferably between 1.0 min and 5.0 min after the base was added, the thus obtained solution is added to the solution containing the amino-modified nucleic acid molecule, preferably between 1.0 min to 5.0 min after the base was added, the solution comprising the condensing agent and the base is added to the solution containing the amino-modified nucleic acid molecule.

In a twelfth embodiment of the first aspect which is also an embodiment of the ninth, tenth and eleventh embodiment of the first aspect, the condensing agent is selected from the group comprising a) phosphonium salts such as BOP, PyBOP, PyBrop, AOP, PyAOP, BrOP and PyClOP, b) uronium salts, such as HCTU, TCTU, TBTU, HBTU, HATU, TOTU and COMU, and c) carbodiimides, wherein preferably the condensing solvent is PyBOP, TBTU, COMU, HBTU, more preferably HBTU.

In a $13^{th}$ embodiment of the first aspect which is also an embodiment of the twelfth embodiment of the first aspect, the carbodiimide is selected from the group comprising DCC (N,N'-dicyclohexylcarbodiimide), EDC (1-ethyl-3-(3-dimethylaminopropyl)carbodiimide) and DIC (N,N'-diisopropylcarbodiimide).

In a $14^{th}$ embodiment of the first aspect which is also an embodiment of the first, second, third, fourth, fifth, sixth, seventh, eighth, ninth, tenth, eleventh, twelfth and $13^{th}$ embodiment of the first aspect, the water miscible organic solvent is selected from the group comprising methanol, ethanol, n-propanol, isopropanol, n-butanol, sec-butanol, tert-butanol, dimethyl sulfoxide, diethyl sulfoxide, methyl ethyl sulfoxide, formamide, methyl formamide, dimethyl formamide, ethyl formamide, ethyl methyl formamide, diethyl formamide, 2-pyrrolidone, N-methyl pyrrolidone, N-ethylpyrrolidone, acetonitrile, acetone, ethyl methyl ketone, methyl propyl ketone, diethyl ketone, methyl isopropyl ketone, methyl formate, ethyl formate, propyl formate, isopropyl formate, methyl acetate, ethyl acetate, methyl propanoate, tetrahydrofuran and dioxan, preferably dimethyl formamide, acetonitrile and dimethyl sulfoxide.

In a $15^{th}$ embodiment of the first aspect which is also an embodiment of the first, second, third, fourth, fifth, sixth, seventh, eighth, ninth, tenth, eleventh, twelfth, $13^{th}$ and $14^{th}$ embodiment of the first aspect, the base is selected from the group comprising diisopropylethylamine (DIPEA), trimethylamine and DBU, preferably diisopropylethylamine (DIPEA).

In a $16^{th}$ embodiment of the first aspect which is also an embodiment of the ninth, tenth, eleventh, twelfth, $13^{th}$, $14^{th}$ and $15^{th}$ embodiment of the first aspect, a or the molar ratio of the base to the first reactant is equal to or greater than 1.

In a $17^{th}$ embodiment of the first aspect which is also an embodiment of the ninth, tenth, eleventh, twelfth, $13^{th}$, $14^{th}$, $15^{th}$ and $16^{th}$ embodiment of the first aspect, the solution of the amino-modified nucleic acid molecule contains a base, preferably a non-nucleophilic base, whereby preferably the molar ratio of the non-nucleophilic base to the number of phosphodiesters in the amino-modified nucleic acid molecule is greater than 3.

In an $18^{th}$ embodiment of the first aspect which is also an embodiment of the first, second, third, fourth, fifth, sixth, seventh, eighth, ninth, tenth, eleventh, twelfth, $13^{th}$, $14^{th}$, $15^{th}$, $16^{th}$ and $17^{th}$ embodiment of the first aspect, step a) is carried out at a temperature of 5° C. to 60° C., preferably at a temperature of 10° C. to 40° C., more preferably at a temperature of 15° C. to 30° C., most preferably at ambient temperature.

In a $19^{th}$ embodiment of the first aspect which is also an embodiment of the first, second, third, fourth, fifth, sixth, seventh, eighth, ninth, tenth, eleventh, twelfth, $13^{th}$, $14t^{h}$, $15^{th}$, $16^{th}$, $17^{th}$ and $18^{th}$ embodiment of the first aspect, step b) is carried out at a temperature of 5° C. to 60° C., preferably at a temperature of 10° C. to 40° C., more preferably at a temperature of 15° C. to 30° C., most preferably at ambient temperature.

In a $20^{th}$ embodiment of the first aspect which is also an embodiment of the first, second, third, fourth, fifth, sixth, seventh, eighth, ninth, tenth, eleventh, twelfth, $13^{th}$, $14^{th}$, 15th, 16th, 17th, 18th and 19th embodiment of the first aspect, reaction of the activated carboxyl group of the first reactant with the amino group of the amino-modified nucleic acid molecule is completed after 5 minutes to six hours, preferably after 15 minutes to 45 minutes, more preferably after 15 to 30 minutes.

In a 21st embodiment of the first aspect which is also an embodiment of the first, second, third, fourth, fifth, sixth, seventh, eighth, ninth, tenth, eleventh, twelfth, 13th, 14th, 15th, 16th, 17th, 18th, 19th and 20th embodiment of the first aspect, step b) is carried at a pH range of 7.5 to 10, preferably at a pH range of 7.5 to 9 and more preferably at a pH range of 7.5 to 8.5.

In a 22nd embodiment of the first aspect which is also an embodiment of the first, second, third, fourth, fifth, sixth, seventh, eighth, ninth, tenth, eleventh, twelfth, 13th, 14th, 15th, 16th, 17th, 18th, 19th, 20th and 21st embodiment of the first aspect, in step b) the activated first reactant is added to the solution of the amino-modified nucleic acid molecules until 80% to 100% of the amino-modified molecules are reacted with the first reactant, preferably until 90% to 100% of the amino-modified nucleic acid molecules are reacted with the first reactant.

In a 23rd embodiment of the first aspect which is also an embodiment of the first, second, third, fourth, fifth, sixth, seventh, eighth, ninth, tenth, eleventh, twelfth, 13th, 14th, 15th, 16th, 17th, 18th, 19th, 20th, 21st and 22nd embodiment of the first aspect, after completion of step b) any non reacted first reactant is separated by ultrafiltration and/or chromatography, preferably by ion exchange chromatography from the reaction.

In a 24th embodiment of the first aspect which is also an embodiment of the 23rd embodiment of the first aspect, the separated first reactant is recycled and used in step a).

In a 25th embodiment of the first aspect which is also an embodiment of the fourth, fifth, sixth, seventh, eighth, ninth, tenth, eleventh, twelfth, 13th, 14th, 15th, 16th, 17th, 18th, 19th, 20th, 21st, 22nd, 23rd and 24th embodiment of the first aspect, the polyalkoxy compound is a straight or branched polyalkoxy compound.

In a 26th embodiment of the first aspect which is also an embodiment of the fourth, fifth, sixth, seventh, eighth, ninth, tenth, eleventh, twelfth, 13th, 14th, 15th, 16th, 17th, 18th, 19th, 20th, 21st, 22nd, 23rd, 24th and 25th embodiment of the first aspect, the polyalkoxy compound is selected from the group comprising polyethylene glycol, polypropylene glycol, poly butylene glycol, polyglycerol.

In a 27th embodiment of the first aspect which is also an embodiment of the fourth, fifth, sixth, seventh, eighth, ninth, tenth, eleventh, twelfth, 13th, 14th, 15th, 16th, 17th, 18th, 19th, 20th, 21st, 22nd, 23rd, 24th, 25th and 26th embodiment of the first aspect, the polyalkoxy compound is polyethylene glycol.

In a 28th embodiment of the first aspect which is also an embodiment of the fourth, fifth, sixth, seventh, eighth, ninth, tenth, eleventh, twelfth, 13th, 14th, 15th, 16th, 17th, 18th, 19th, 20th, 21st, 22nd, 23rd, 24th, 25th, 26th and 27th embodiment of the first aspect, the polyalkoxy compound has a molecular weight of 5,000 Da to 100,000 Da, preferably of 20,000 Da to 80,000 Da, more preferably 40,000 Da.

The problem underlying the present invention is solved in a second aspect by a modified nucleic acid molecule obtained by a method according to the first aspect, including any embodiment thereof.

The problem underlying the present invention is solved in a third aspect by a modified nucleic acid molecule obtained by a method according to the first aspect, including any embodiment thereof, for use in therapy.

The problem underlying the present invention is solved in a fourth aspect by a modified nucleic acid molecule obtained by a method according to the first aspect, including any embodiment thereof, for use in diagnosis.

The problem underlying the present invention is solved in a fifth aspect by the use of a modified nucleic acid molecule obtained by a method according to the first aspect, including any embodiment thereof, in an in vitro method for analyzing a sample.

The present invention is based on the surprising identification of an improved protocol for the polyalkoxylation of amino-modified oligonucleotides that allows a more efficient production of polyalkoxylated nucleic acids as known from the state of the art (Hoffmann et. al, *Current Protocols in Nucleic Acid Chemistry* 2011, 4:4.46.1-4.46.30). The present invention provides in particular a method for the preparation of polyalkoxylated nucleic acids which comprises reacting an amino-modified nucleic acid with a polyalkoxycarboxylic acid activated with a condensation reagent just prior to the conjugation reaction. Additionally, it was surprisingly found, that polyalkoxycarboxylic acid used in excess to drive the reaction to completion, could be recovered during the down-stream processing such as by means of UF and/or HPLC purification of the crude polyalkoxylation product. After drying, the recycled polyalkoxycarboxylic acid was reusable for another polyalkoxylation reaction.

The method of the present invention goes along with various advantages compared to the methods of the prior art. More specifically, the method of the invention is less laborious and is a more environmental friendly manufacturing process enabling recycling of the first reactant bearing the carboxyl group which is used in excess. Also, the preparation of the first reactant bearing the carboxyl group is requiring less manufacturing steps and is thus less laborious than the preparation and isolation of the activated carboxyl reactant which has been described in the prior art. Also, the first reactant bearing the carboxyl group is more stable than the activated carboxyl moiety described in the prior art and doesn't require special cold storage conditions which adds to the advantageous of the method of the invention.

In light of the above and in accordance with the present invention, the polyalkoxycarboxylic acid itself can be used as a starting material for the reaction with the amino-modified nucleic acid molecule such as an amino-modified oligonucleotide, so as to form the modified nucleic acid molecule and the modified oligonucleotide, respectively, whereby the modification is preferably a polyalkoxy moiety and more preferably a PEG moiety.

In an embodiment of the method of the invention, the activated first reactant as prepared in step a) of the method of the invention is reacted with the amino-modified nucleic acid molecule, whereby the reaction occurs in a solution; the elements of such solution comprise said activated first reactant and said amino-modified nucleic acid molecule and a solvent, whereby the solvent is selected from the group comprising water and a mixture of a water miscible organic solvent and water. Preferably, the activated first reactant and/or the amino modified nucleic acid molecule are dissolved or dispersed in the solvent or a part of such solvent. As preferably used herein, a part of the solvent is one phase of the solvent or one of the phases formed by the solvent.

In an embodiment of the method of the invention, the activated first reactant is added to the amino-modified nucleic acid, whereby, preferably, the amino-modified nucleic acid is present in the solution. In an alternative embodiment, the amino-modified nucleic acid, which is preferably present in the solution is added to the first activated reactant, preferably the first activated reactant of step a).

In an embodiment of the method of the invention, the nucleic acid moiety comprises a nucleic acid molecule.

In an embodiment of the method of the invention, the non-nucleic acid moiety is bearing a carboxyl group.

In an embodiment of the method of the invention, the amino-modified nucleic acid molecule comprises the nucleic acid moiety and an amino modification which is attached to the nucleic acid moiety.

In an embodiment of the method of the invention, the amino-modified nucleic acid molecule has been dissolved in water or a mixture of a water miscible organic solvent and water, prior to reacting the amino-modified nucleic acid molecule with the first reactant. Accordingly, the solution in which the amino-modified nucleic acid molecule is present prior and after the reaction with the first reactant is different, also with regard to the solution and the solvents forming such solution.

In an embodiment and as preferably used herein, a carbohydrate moiety is a moiety comprising a carbohydrate or a polymer of carbohydrates. A carbohydrate moiety includes, but is not limited to, a carbohydrate, a polymer of carbohydrates, a glycoprotein, a nucleotide and a nucleic acid.

In an embodiment of the method of the invention, the amino-modified immunostimulatory nucleic acid is an amino-modified immunostimulatory nucleic acid.

In an embodiment of the method of the invention, the immunostimulatory nucleic acid is an immunostimulatory nucleic acid.

In an embodiment of the method of the invention, an aptamer is a target binding nucleic acid which preferably binds to the target through a binding different from Watson-Crick base pairing or Hoogsteen base pairing. Preferably, the aptamer consists of D-nucleotides. In an alternative embodiment, the aptamer is a mixed aptamer which comprises both D-nucleotides and at least one L-nucleotide, whereby preferably the number of L-nucleotides in the aptamer is lower than the number of D-nucleotides.

In an embodiment of the method of the invention, a Spiegelmer is a target binding nucleic acid of L-nucleotides which preferably binds to the target through a binding different from Watson-Crick base pairing or Hoogsteen base pairing. Preferably, the Spiegelmer consists of L-nucleotides. In an alternative embodiment, the Spiegelmer is a mixed Spiegelmer which comprises both L-nucleotides and at least one D-nucleotide, whereby preferably the number of D-nucleotides in the aptamer is lower than the number of L-nucleotides.

Both aptamers and Spiegelmers may by modified. Such modification may be related to a single nucleotide of the nucleotide sequence of such aptamers and Spiegelmers and are well known in the art. Examples for such modification are described by, among others, Venkatesan et al. (Venkatesan, N., Kim, S. J., et al., Curr. Med. Chem. 10, 1973 (2003)) and Kusser (Kusser, W., J. Biotechnol. 74, 27 (2000)). Such modification can be an H atom, an F atom or an $OCH_3$ group or $NH_2$-group at the 2' position of the individual nucleotide of which the aptamer consists. Also, the aptamer according to the present invention can comprise at least one locked nucleotide (LNA) or unlocked nucleotide (UNA).

In an embodiment and as preferably used herein, ambient temperature means 20° C. to 22° C.

In an embodiment of the method of the invention, the amino-modified nucleic acid molecule comprises an amino group; preferably, the amino group can be reacted with a carboxyl group, preferably an activated carboxyl group.

In an embodiment of the method of the invention, an activated first reactant is a first reactant which has been subject to activation by means of a condensation reagent; preferably, the activated first reactant is a first reactant comprising an activated carboxyl group, whereby the activated carboxyl group results from a carboxyl group of the first reactant having been subjected to activation by means of a condensation reagent.

The quaternary ammonium salt used in an embodiment of the method of the invention, is used to enhance the solubility of the amino-modified nucleic acid molecule in the mixture of water and a water miscible organic solvent. It is selected from the group comprising tetraalkyl ammonium chloride, tetraalkyl ammonium bromide, tetraalkyl ammonium tertrafluoro borate, tetraalkyl hexafluoro phosphate, tetraalkyl hydrogen sulphate, tetraalkyl hydrogen phosphate, wherein alkyl is an alkyl chain consisting of 1, 2, 3, 4, 5, 6, 7, 8, 9, 10, 11, 12, 13,14, 15, 16, 17 or 18 C-atoms, wherein preferably the quaternary ammonium compound is tetrabutyl ammonium bromide.

In an embodiment of the method of the invention, fatty acids include saturated and unsaturated fatty acids with one or several double bonds. Both, saturated and unsaturated fatty acids can have a chain length of 8 to 30 carbon atoms, i.e. a length of 8, 9, 10, 11, 12, 13, 14, 15, 16, 17, 18, 19, 20, 21, 22, 23, 24, 25, 26, 27, 28, 29 or 30 carbon atoms.

In an embodiment of the method of the invention, steroids include corticosteroids such as cholesterol, bile acids such as cholic acid and lithocholic acid, steroid hormones such as cortisol or progesterone, steroid glycosides such as digoxigenin, and metabolites of aforementioned steroids.

In an embodiment of the method of the invention, the base and preferably the non-nucleophilic base is selected from the group comprising trialkylamines such as diisopropylethylamine (DIPEA), trimethylamine, triisopropylamine, peralkylated sterically hindered polyaminophosphazenes bases such as t-Bu-P4,1,8-diazabicycloundec-7-ene (DBU), 2,6-Di-tert-butylpyridine, 1,8-bis(dimethylamino)naphthalene, lithium tetramethylpiperidide, potassium tert-butoxide, 1,1, 3,3-tetramethylguanidine, 2,2,6,6-tetramethylpiperidine. In a preferred embodiment, the base is diisopropylethylamine (DIPEA).

The polyalkoxylation method of the invention can be applied to nucleic acids containing natural sugar moieties, for example 2'-deoxyribonucleic acids (hereinafter "DNA") and ribonucleic acids (hereinafter "RNA") and nucleic acids containing modified sugar moieties, modified phosphate moieties, or modified nucleobases. The method according to the invention is not restricted to the natural stereoisomer of RNA and DNA. Also, polyalkoxylated nucleic acids comprising mirror image DNA (L-DNA) or RNA (L-RNA) as well as sugar-, phosphate- or nucleotide-modified L-DNA or L-RNA as well as D/L-hybrid oligonucleotides and modifications thereof can be prepared by the method according to the present invention. Modifications to the sugar moiety include the change of the ring size (e.g., furanose, hexose), replacement, introduction or removal of single ring atoms (e.g., carba sugars, aza sugar), replacement, introduction or removal of side chain groups or atoms (e.g., 2'-F, 2'OMe), replacement of the ring by acyclic or poly cyclic derivatives (e.g., unlocked nucleic acid, amino acid nucleic acid, locked nucleic acid, tricycle nucleic acid), orientation or position of the nucleobase (α-anomeric orientation, hexitol nucleic acid). The oligonucleotide may also consist of one or more natural or non-natural abasic moieties (e.g., tetrahydrofurane, ethylene glycol). Modified phosphate moieties include phosphorothioates, phosphorodithioates, alkylphosphonates, alkylphosphates, phosphoramidates and phosphorthioamidates. Modifications of the nucleobases can be naturally occurring such as inosine, xanthine, 5,6-dihydrouracil or 5-methylcytosine or artificial modifications such as C5-alkynylpyrimidines, N-alkylated purines and pyrimidines, C6- and/or C5-derivatives of pyrimidines and purines and others. The nucleic acid may also comprise or consist of one or more of the above-named modification.

Methods for the assembly of nucleic acids are well known in the art. In embodiments, the nucleic acids will be assembled by the phosphoramidite method employing a stepwise coupling of protected building blocks to the nascent nucleic acid on a solid support (Beaucage et. al., *Tetrahedron* 1992, 48(12), 2223-2311). In a preferred embodiment, synthesis direction is from 3' to 5' direction, but also reverse synthesis from 5' to 3' direction is applicable (Srivastava et. al. *Nucleic Acids Symposium Series* 2008, 52, 103-104). Once the desired nucleic acids sequence is assembled and all necessary modifications for downstream processing are introduced, the nucleic acid is cleaved from the solid support and deprotected. The nucleic acids may then be purified by any of the means known in the art.

Commonly, the cleavage and deprotection step involves the usage of ammonia and/or alkylamine or ammonia salts. For example, RNA is cleaved with $NH_3$/$MeNH_2$ followed by $NEt_3$.HF or $Bu_4NF$. In case of subsequent polyalkoxylation, these amines and ammonium salts have to be removed as they lead to unwanted side reactions lowering the coupling efficacy during polyalkoxylation. The removal of amine species is achieved by salt exchange which can be done by addition of large quantities of sodium salts followed by precipitation or ultrafiltration, or during IEX-HPLC by using sodium salt gradients for elution. After IEX-HPLC purification the removal of excess salt prior to polyalkoxylation is also necessary. A plurality of different techniques can be applied, if necessary. In preferred embodiments salt exchange followed by ultrafiltration is used prior to polyalkoxylation. The position of the amino-modification in the second reactant and preferably in the amino-modified nucleic acid molecule such as, e.g., an oligonucleotide, can be on the 3'-end and/or at the 5'-end and/or at any position between the 3' terminal nucleotide and the 5' terminal nucleotide of the second reactant and preferably of the amino-modified nucleic acid molecule such as, e.g., an oligonucleotide. The amino modified nucleic acids used for the examples to illustrate the present invention were synthesized and purified according to examples 1-3.

Polyalkoxy compounds which can be used in the present invention include poly(ethylene oxides), poly(propylene oxides) and mixed poly(ethylene oxide)/poly(propylene oxide) compounds. The polyalkoxy compounds are preferably of the formula: $P_rO$—$(CH_2CH_2O$—$)_x$—$(CH_2CHRO$—$)_y$—$(CH_2CH_2O$—$)_z Q$, wherein x, y and z are each independently zero or a positive integer, provided that at least one of x, y and z is not zero; R is H or an alkyl, such as a C1, C2, C3 or C4 alkyl, preferably a methyl, group, $P_r$ is a capping group or a labelling group, and Q is a group permitting coupling with the oligonucleotide. When x, y or z are not zero, they are typically up to 1000. In some embodiments, x is from 3 to 1000, for example from 100 to 500, and both y and z are zero. In other embodiments, x and y are each independently from 3 to 1000, for example from 100 to 500, and z is zero. In yet other embodiments, x and z are each independently from 3 to 500, for example from 100 to 300, and y is from 3 to 1000, for example from 100 to 500. Preferably, the polyalkoxy compound is capped, for example by a C1, C2, C3 or C4 alkyl, preferably a methyl, group. Labelling groups which may be represented by $P_r$ include fluorescein and biotin or also any other reactive group such as, for example, thiol, maleimide, azide or alkyne. The polyalkoxy compounds used are commonly identified by their approximate average molecular weight and abbreviated chemical name (for example, PEG=poly(ethylene glycol); PPG=poly(propylene glycol)). The polyalkoxy compound may be linear or branched, and commonly has an average molecular weight of from about 0.2 kD to about 60 kD, preferably from about 2 kD to about 40 kD. When the polyalkoxy compound is branched, group Q permitting coupling with the oligonucleotide, may carry two or more polyalkoxy moieties. For example, Q may represent a lysine or equivalent moiety carrying two polyalkoxy moieties, and a reactive group. In a preferred embodiment of the method of the invention, group Q permitting coupling with the oligonucleotide comprises a carboxylic acid moiety. Preferably, the polyalkoxy compound is PEG.

Formation of an amide bond between a carboxylic acid and an amine as preferable realized in the method of the invention between the first reactant comprising a carboxyl group and the second reactant, i.e. an amino-modified nucleic acid molecule comprising an amino group, is a condensation reaction, which can be achieved at 160-180° C. (Jursic, B. S.; Zdravkovski, Z. *Synth. Commun.* 1993, 23, 2761-2770). However, high temperature is incompatible with oligonucleotides. Therefore, carboxylic acids are activated for example as esters. Esters of electron withdrawing alcohols such as p-nitrophenol (pNP), pentafluorophenol, N-hydroxysuccinimide (NHS), hydroxybenzotriazole (HOBt) and others display an increased electrophilicity at the carbonyl center, thus making them susceptible for reaction with a wide variety of nucleophiles. In accordance therewith, this kind of alcohols is preferred in embodiments of the method of the invention. They react with amines under mild conditions to yield the desired amide. For the conjugation of polyalkoxycarboxylic acids to biomolecules such as DNA, RNA or proteins most commonly N-hydroxysuccinimide esters (NHS-esters) are used.

Preferably, the reaction of amino-modified oligonucleotides with PEG-NHS-esters is performed in aqueous organic solvents or solutions comprising water and a water miscible organic solvent. Preferred organic solvents are aprotic, polar and include for example DMF, DMSO, NMP or acetonitrile. The concentration of the organic solvent in solutions comprising a water miscible organic solvent can vary from about 10% to about 75%. The nucleic acid such as, for example, the oligonucleotide, is usually used or present in a slightly alkaline aqueous solution which equally applies to the second reactant in general. To achieve the slightly alkaline pH buffers, such as sodium bicarbonate or sodium borate, but also non-nucleophilic tertiary amines bases, such as $NEt_3$ or DIPEA can be used. Preferably, the pH of the oligonucleotide solution is adjusted to 8.5 to 9.5. When using non-nucleophilic amines for buffering, this can be achieved by adding the base in 2- to 5-fold excess over the total number of phosphodiester bridges provided by the oligonucleotide present. The PEG-NHS-ester is used as a solution in a water miscible organic solvent and remains in solution when added to the aqueous solution of the oligonucleotide. Molar ratios of the PEG-NHS-ester and of the oligonucleotide can vary from 1:1 to 5:1 per reactive amino group provided by the oligonucleotide depending on scale and reactivity. Addition of the PEG-NHS-ester preferably continues until completion of the reaction. The reaction can be followed by all analytical techniques available to the skilled person. In embodiments of the invention, RP-HPLC is applied to follow the PEGylation reaction. To achieve best conversion, temperatures may vary from ambient temperature to 45° C.

The aforementioned polyalkoxycarboxylic acid-NHS esters, or more specifically PEG-NHS esters are preferably pre-formed in a separate reaction, and subsequently purified and stored until their usage in the method of the invention. NHS-esters are for example prepared by reaction of a carboxylic acid with NHS in the presence of a condensation agent such as a carbodiimide, e.g., DCC, EDC or DIC. In peptide chemistry, a plethora of condensation agents is available for the amide bond formation between carboxylic acids and amines. The group of condensation agents comprises phosphonium salts, such as BOP, PyBOP, PyBrop, AOP, PyAOP, BrOP and PyClOP, uronium salts, such as HCTU, TCTU, TBTU, HBTU, HATU, TOTU and COMU and many others (C. A. G. N. Montalbetti, V. Falque *Tetrahedron*, 2005, 61, 10827-10852, Ayman El-Faham and Fernando Albericio, *Chem. Rev.*, 2011, 111, (11), 6557-6602) all of which may be used in embodiments of the invention. A condensation agent is a reagent that reacts with a carboxylic acid to form an ester which is of high reactivity towards an amine or other nucleophile, thereby enabling the desired condensation reaction under mild conditions. Amide bond formation in solution and solid phase peptide synthesis is performed in organic solvents with low water content such as DMF, NMP, DMSO, ACN or $CH_2Cl_2$. However, oligonucleotides are not soluble in organic solvents free of water.

The present inventor has additionally surprisingly found that common condensation reagents as mentioned above can be used very efficiently for the activation of PEGcarboxylic acid (PEG-COOH) in the context of preparing PEGylated oligonucleotides, if the activation of PEG-COOH with the condensation reagent is performed in a water miscible organic solvent over a period of 0.5 min to 60 min, preferably 1 to 20 min., which is followed by addition of the activated PEG to the amino-modified oligonucleotide in water (see, Examples 4-10). FIG. 3 shows a typical chromatogram of crude 5'-aminomodified L-RNA Spiegelmer NOX-E36 (5'-$NH_2$-NOX-E36, Table 1, entry 1) prior to PEGylation when analysed by A) IEX-HPLC and C) by RP-HPLC. A typical chromatogram of crude 5'-$NH_2$-NOX-E36 after PEGylation with 40 kDa PEG-COOH and the condensing reagent HBTU is shown in FIGS. 3B and 3D, respectively (example 9). In the shown examples, RP-HPLC analysis indicates full conversion if the percentage of the UV-area of the later eluting product peak is equal or slightly higher as the percentage of full length product content of the 5'-amino modified oligonucleotide found by IEX-HPLC. For example, the crude 5'-$NH_2$-NOX-E36 used in Examples 4-10 shows a purity of 47% full length product by IEX-HPLC. The crude product contains up to 15% amino modified species not having the desired nucleotide sequence such as failure and addition sequences, which are also PEGylateable. Hence, in this case up to 60% UV-area of product peak by RP-HPLC can be attributed to full conversion (example 5).

Comparable results were achieved when PyBOP, TBTU or COMU were used (examples 4-7). Also, carboxylic acids of small molecules were demonstrated to be efficiently coupled to amino-modified oligonucleotides. As shown in example 11 biotin was activated and coupled to 5'-$NH_2$-NOX-A12 (Table 1, entry 2) with very high efficacy. The IEX-HPLC analysis of crude 5'-$NH_2$-NOX-A12 prior to biotinylation using HBTU for pre-activation is shown in FIG. 4A. The LC-MS and IEX-HPLC analysis of the resulting crude 5'-biotin-NOX-A12 is shown in FIG. 4B and 4C and verifies the correct molecular weight and shift in retention time expected for the biotinylated product.

Further, the present inventor has surprisingly found that excess PEG-COOH such as 40 kDa PEG-COOH used to drive the PEGylation reaction to completion can be recovered from the crude reaction mixture either by ultrafiltration (Example 12) or during IEX-purification (Example 15) of the crude PEGylated oligonucleotide. After removal of small molecules contained in the reaction such as condensation reagent, organic solvents or salts by UF and subsequent drying (Example 16) the recovered PEG-COOH could be reused for the PEGylation of an amino-modified oligonucleotide (Example 18, 19 and 22). The IEX-HPLC analysis of crude 5'-$NH_2$-NOX-A12 prior to PEGylation is shown in FIG. 5A. A typical IEX-chromatogram of crude NOX-A12 after PEGylation with "fresh" PEG-COOH is shown in FIG. 5B. A typical IEX-chromatogram of the resulting purified PEGylated NOX-A12 product is shown in FIG. 5C. The recycled 40 kDa PEG-COOH showed a similar high conjugation efficacy compared to "fresh" PEG-COOH (Example 18, 19 and 17, respectively). The yield and quality of the PEGylated product was equally high for "fresh" and recycled 40 kDa PEG. FIGS. 5C and 5E show a typical IEX-HPLC analysis of purified PEGylated NOX-A12 after PEGylation with "fresh" and "recycled" 40 kDa PEG-COOH, respectively.

The present invention proves to be superior as it uses polyalkoxycarboxylic acids instead of polyalkoxycarboxylic acid NHS-esters for the polyalkoxylation of amino-modified nucleic acid molecules such as oligonucleotides. The method is superior because it does not require any intermediate production and isolation of any activated NHS-ester from the polyalkoxycarboxylic acid, thereby reducing the number of overall reaction steps. Also, the polyalkoxycarboxylic acid is more stable and easier to store than moisture-sensitive polyalkoxycarboxylic acid NHS esters. Furthermore, the method of the invention enables the economic re-use of reagents which are typically used in excess to drive the reaction to completion.

In accordance therewith and in an embodiment of the method of the invention, after completion of step b) in its various embodiments, any non-reacted first reactant is separated from the reaction, preferably by means of ultrafiltration and/or chromatography, preferably ion exchange chromatography. Depending on the nature of the excess of the first reactant, non-reacted material, i.e. non-reacted first reactant may be separated from the nucleic acid molecule and more specifically from the modified nucleic acid molecule by ultrafiltration (UF) or chromatography, preferably from the desired modified nucleic acid molecule. UF is the method of choice when there is a sufficiently large difference in hydrodynamic volume, related to molecular weight, between the first reactant and the unmodified and modified nucleic acid molecule. Alternatively, ion-exchange (IEX HPLC) or reverse phase (RP HPLC) chromatography might be used in case of charge or lipophilicity differences between the first reactant and the unmodified and modified nucleic acid molecule. In case of uncharged (neutral) first reactants such as polyalkoxy compounds, steroids, carbohydrates and fatty acids IEX-HPLC is the method of choice, since the resin has a weaker affinity for the first reactant than for the nucleic acid. In case of amphiphilic peptides, proteins or glycoproteins IEX-HPLC or RP-HPLC might be employed.

It is within the present invention that a nucleic acid is a nucleic acid molecule. Insofar the terms nucleic acid and nucleic acid molecule are used herein in a synonymous manner if not indicated to the contrary. Moreover, such nucleic acid(s) is/are preferably also referred to herein as the nucleic acid molecule(s) according to the present invention, the nucleic acid(s) according to the present invention, the inventive nucleic acid(s) or the inventive nucleic acid molecule(s). Additionally, it is within the present invention that a nucleic acid is an oligonucleotide. In light thereof, it is to be acknowledged that the disclosure of the instant application to the extent it refers to an oligonucleotide, equally applies to any nucleic acid, and vice versa, as long as not explicitly stated differently. Also, any discourse presented herein related to the use of an oligonucleotide in the method of the invention equally applies to the first reactant and its use in the method of the invention.

In another aspect, the present invention is related to a modified nucleic acid molecule obtained by a method of the present invention.

In a further aspect, the present invention is related to a modified nucleic acid molecule obtained by a method of the invention, for use in therapy. Such use in therapy comprises the administration of the modified nucleic acid molecule to a subject in need thereof. Such subject is preferably a human which is suffering from a disease or at risk of suffering from a disease. In such use, the modified nucleic acid molecule is capable of treating such disease or preventing such disease.

In a still further aspect, the present invention is related to a modified nucleic acid molecule obtained by a method of the invention, for use in diagnosis. Such diagnosis may be an in vivo diagnosis or in vitro diagnosis. In case of in vivo diagnosis, the modified nucleic acid molecule is administered to a subject to be diagnosed. Such subject is preferably a human which is suffering from a disease, at risk of suffering from a disease or suspected of suffering from or developing such disease. In such use, the modified nucleic acid molecule is capable of binding to a biomarker associated with disease.

Finally, the present invention is related in another aspect to the use of a modified nucleic acid molecule obtained by a method of the invention in an in vitro method for analyzing a sample. Such analyzing of the sample is intended to detect the presence or absence of an analyte. For such used, the nucleic acid molecule is capable of binding to the analyte.

It will be acknowledged by a person skilled in the art. That analytical and diagnostic applications of the modified nucleic acid molecule obtained by the method of the invention may encompass methods of in vitro or in vivo hybridisation of nucleic acids, or in vitro or in vivo binding of the nucleic acid to the target molecule in the case of aptamers, and detection of the hybridized or bound nucleic acid by means of radioactivity, light absorbance or emittance.

Synthetic applications include the use of nucleic acids in asymmetric catalysis, nucleic acid encoded libraries, and affinity chromatography.

It will be acknowledged by the ones skilled in the art that the nucleic acid in accordance with the invention preferably consists of nucleotides which are covalently linked to each other, preferably through phosphodiester links or linkages. Other links or linkages present in a nucleic acid molecule as subject to the present invention are phosphothioate links and linkages, respectively, and phosphoamidate links and linkages, respectively.

It is to be acknowledged that the terms condensating agent and condensing agent are used synonymously herein.

It is to be acknowledged that the terms "of the invention" and "of the present invention" are used synonymously herein.

It is to be acknowledged that any percentages indicated herein are volume/volume (v/v).

The present invention is further illustrated by the table, figures and examples from which further features, embodiments and advantages may be taken, wherein FIG. 1 shows a schematic drawing of a method according to the present invention;

TABLE 1

Figure 1:
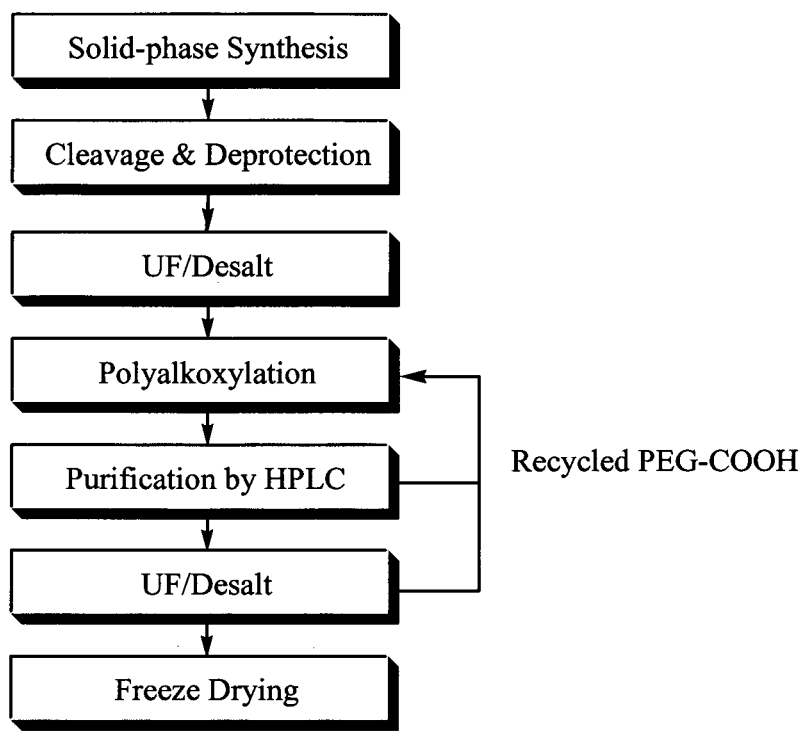
Figure 2:
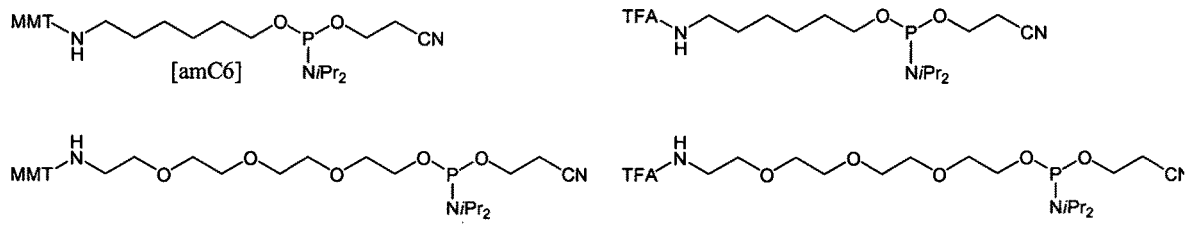
FIG. 2 shows reagents enabling for the introduction of reactive amino-groups into the nucleic acids.
Figure 2:
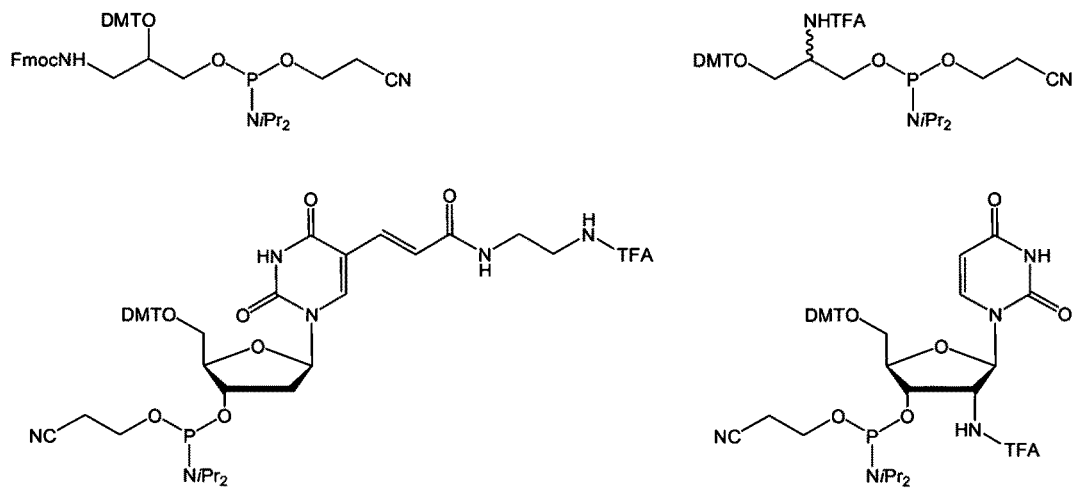
Figure 2:
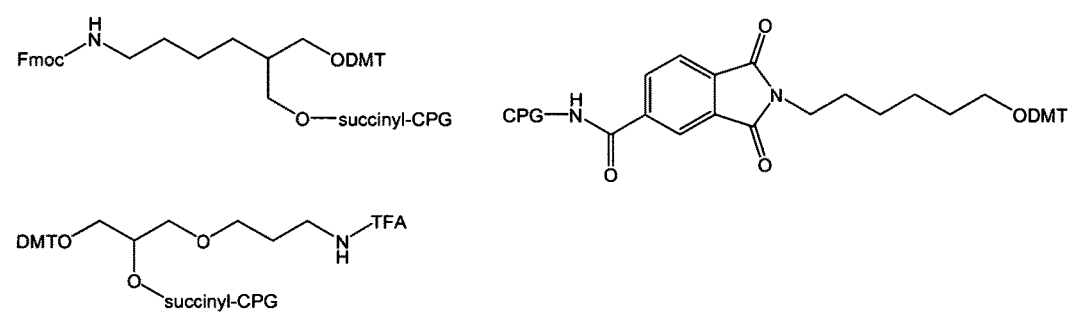
Figure 3:
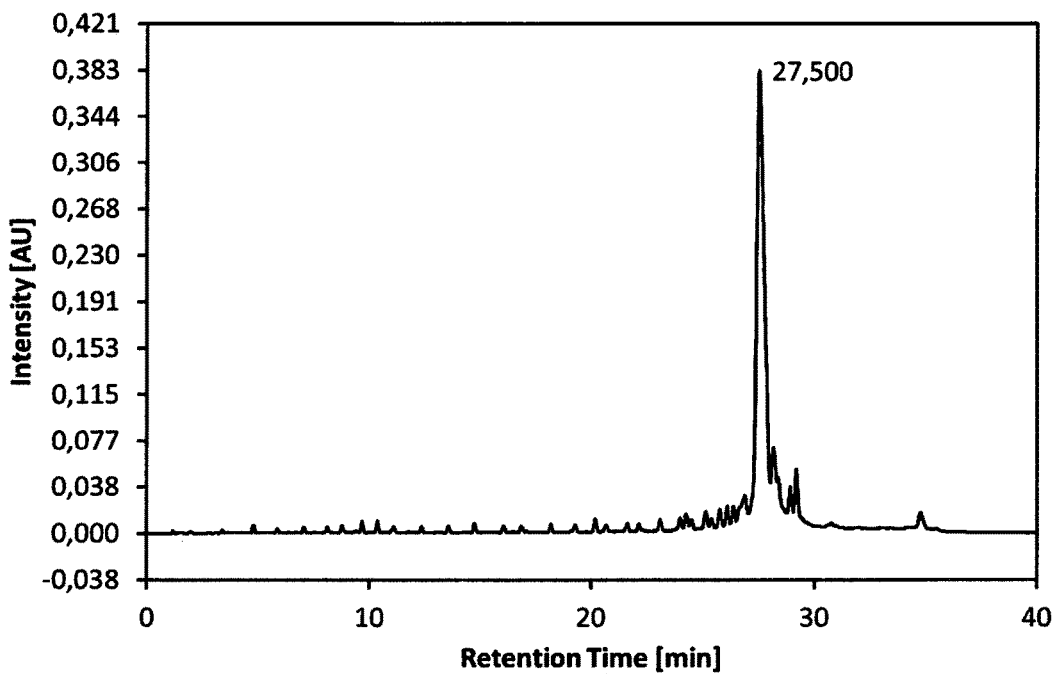
FIG. 3A shows the IEX-HPLC analysis of typical crude synthesis product of 5'NH$_2$-NOX-E36 prior to PEGylation.
FIG. 3B shows the IEX-HPLC analysis of typical crude synthesis product of 5'NH$_2$-NOX-E36 after PEGylation.
FIG. 3C shows the RP-HPLC analysis of typical crude synthesis product of 5'NH$_2$-NOX-E36 prior to PEGylation.
FIG. 3D shows the RP-HPLC analysis of typical crude synthesis product of 5'NH$_2$-NOX-E36 after PEGylation.
Figure 3:
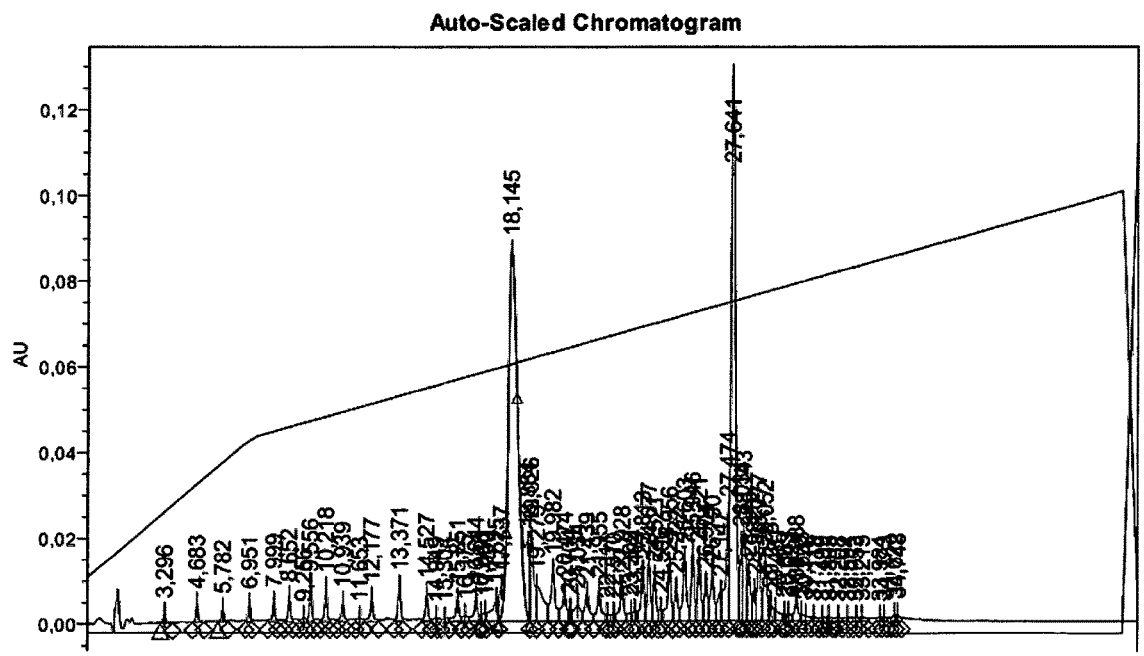
Figure 4:
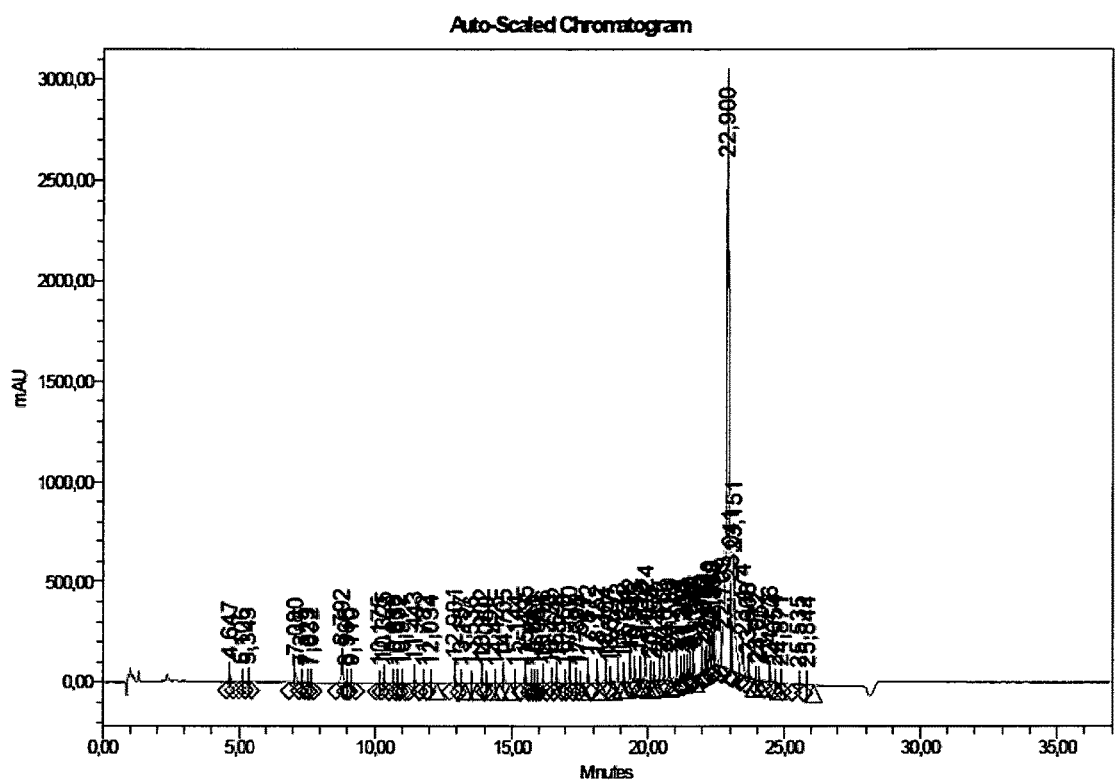
FIG. 4A shows the IEX-HPLC analysis of typical crude synthesis product of 5'NH$_2$-NOX-A12 prior to conjugation.
FIG. 4B shows the LCMS analysis of typical crude synthesis product of 5'NH$_2$-NOX-A12 after Biotin conjugation.
FIG. 4C shows the IEX-HPLC analysis of typical crude synthesis product of 5'NH$_2$-NOX-A12 after Biotin conjugation.
Figure 4:
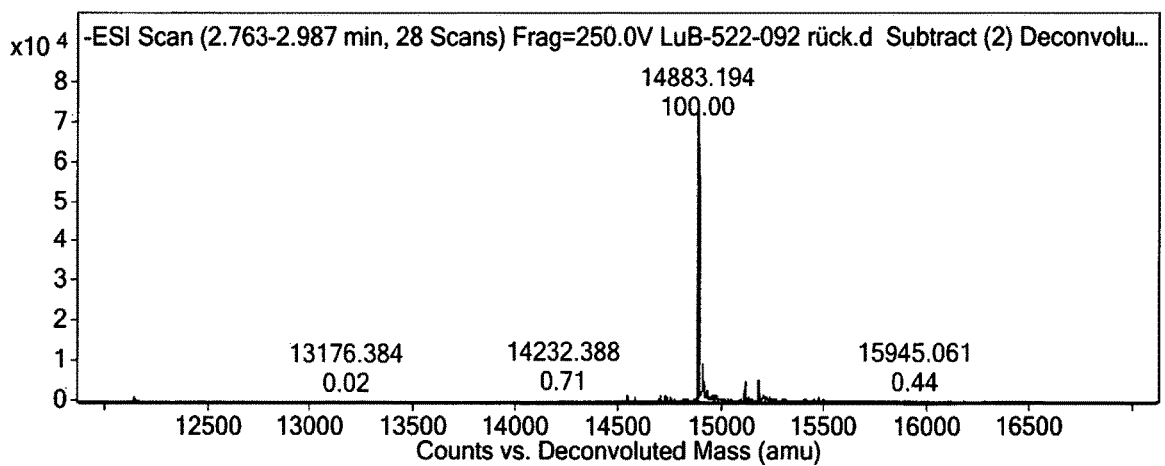
Figure 5:
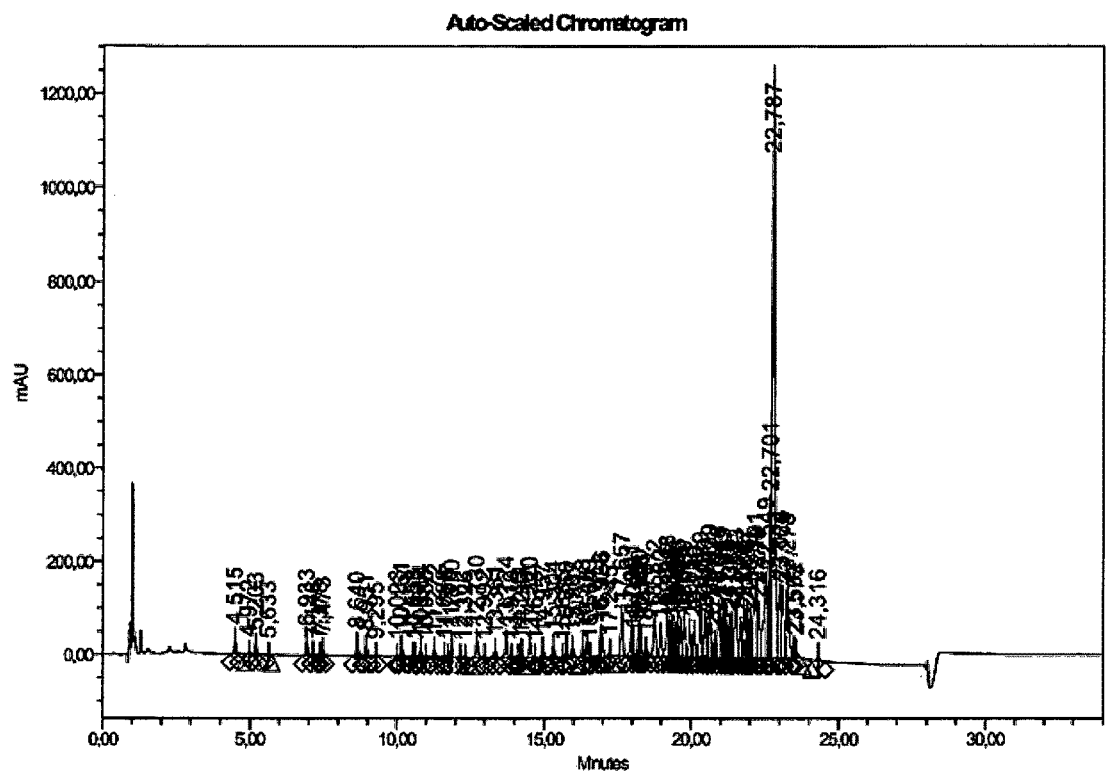
FIG. 5A shows the IEX-HPLC analysis of typical crude synthesis product of 5'NH$_2$-NOX-A12 prior to PEGylation.
FIG. 5B shows the IEX-HPLC analysis of typical crude product of 5'NH$_2$-NOX-A12 after PEGylation with "fresh" PEG.
FIG. 5C shows the IEX analysis of typical purified product of 5'NH$_2$-NOX-A12 after PEGylation with "fresh" PEG.
FIG. 5D shows the IEX-HPLC analysis of typical crude product of 5'NH$_2$-NOX-A12 after PEGylation with "recycled" PEG.
FIG. 5E shows the IEX analysis of typical purified product of 5'NH$_2$-NOX-A12 after PEGylation with "recycled" PEG.
Figure 5:
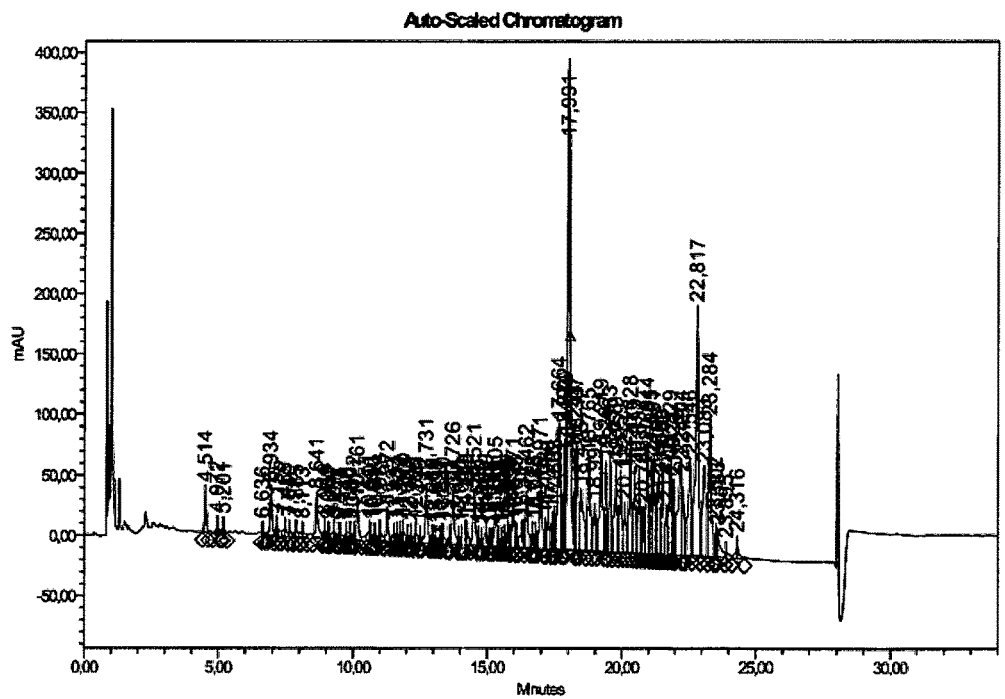

Sequences of nucleic acids used to demonstrate the method according to the present invention
Table 1

| No | Sequence | Length | Modification Type | Name |
|---|---|---|---|---|
| 1 | 5'-rG-rC-rA-rC-rG-rU-rC-rC-rC-rU-rC-rA-rC-rC-rG-rG-rU-rG-rC-rA-rA-rG-rU-rG-rA-rA-rG-rC-rC-rG-rU-rG-rG-rC-rU-rC-rU-rG-rC-rG-3' | 40 nt | L-RNA 5' 40 kDa PEG via aminohexyl-linker | NOX-E36 |
| 2 | 5'-rG-rC-rG-rU-rG-rG-rU-rG-rU-rG-rA-rU-rC-rU-rA-rG-rA-rU-rG-rU-rA-LrU-LrU-LrG-LrG-LrC-LrU-LrG-LrA-LrU-LrC-rC-LrU-rA-rG-rU-rC-LrA-rG-rG-rU-rA-LrC-rG-rC-3' | 45 nt | L-RNA 5' 40 kDa PEG via aminohexyl-linker | NOX-A12 |

EXAMPLE 1

RNA Synthesis

RNA Spiegelmers were produced by solid-phase synthesis using an AktaPilot100 synthesizer (GE Healthcare, Freiburg) in a 48 mL fixed volume column using 2'-TBDMS RNA phosphoramidite chemistry (Damha and Ogilvie, *Methods in Molecular Biology*, 1993, 81-114, The Humana Press Inc., Totowa, N.J.). L-rA(N-Bz)-, L-rC(Ac)-, L-rG(N-ibu)-, and L-rU-phosphoramidites were purchased from ChemGenes (Wilmington, Mass., USA). The 5'-amino-modifier amC6 was purchased from ChemGenes (Wilmington, Mass., USA). Synthesis of the amino-modified Spiegelmer was started on L-riboG, or L-riboC modified CPG pore size 600 Å (Prime Synthesis, Aston, Pa., USA). As an alternative 3'amino(TFA) modified CPG pore size 1000 Å (ChemGenes, Wilmington, Mass., USA) could have been used. For coupling (12 min per cycle), 0.6 M ethylthiotetrazole (Azide Chemical Co., Ltd, Anzhen, Wuxi, CN) in acetonitrile and 1.5-4 equivalents of the respective 0.2 M phosphoramidite solution in acetonitrile were used. A capping-oxidation cycle was used. Standard solvents and reagents for oligonucleotide synthesis were purchased from Biosolve (Valkenswaard, NL), Proligo (Hamburg, D), VWR (Karlsruhe, D) or Sigma Aldrich (Taufkirchen, D). The Spiegelmers were synthesized 5'-MMT-ON. Cleavage and deprotection was achieved according to Wincott et al. (Wincott, *Nucleic Acids Research* 1995, 23(14), 2677-2684) with minor alterations. In detail, upon completion of the automated synthesis, the CPG-bound oligonucleotide (700 µmol) was briefly dried and transferred into a glass bottle. 200 mL of aq. MeNH$_2$ (40%) were added, and the suspension was gently agitated at room temperature. After 90 min. the slurry was filteredand the residual CPG washed several times with aq. EtOH (50%). The combined filtrates were concentrated and finally lyophilized to dryness. For the removal of the 2'-TBDMS groups, the dry crude product was dissolved in 120 mL of DMSO followed by 60 mL of NEt$_3$ and 80 mL of NEt$_3$.3HF. This mixture was gently agitated at 65° C. for 2 h. After cleavage of the 2'-TBDMS groups, the reaction was quenched by addition of 1 L of ice water. Removal of the MMT-group was assisted by addition of acetic acid (25 mL). Subsequently, the Spiegelmer was desalted by tangential-flow filtration using a 2 kDa regenerated cellulose membrane (Sartorius, Göttingen, D). For salt exchange 3 L of 0.25 M NaCl solution were added and the solution was desalted by tangential-flow filtration. Finally, the product was harvested and dried by lyophilization.

EXAMPLE 2

Synthesis of 5'NH$_2$-NOX-E36 (1 prePEG)

Applying the procedure described in Example 1, 10.2 g of L-rG CPG (600 Å, 70 µmol/g, 711 µmol) were used to assemble 5'NH$_2$-NOX-E36 (1 prePEG) with 2 eq. of amidite per nucleotide coupling cycle. Yield after UF: 150732 OD, Purity: 47%, Mass: 12997 Da (found), 12996 Da (calc.).

EXAMPLE 3

Synthesis of 5'NH$_2$-NOX-A12 (2 prePEG)

Applying the procedure described in Example 1, 1.7 g of L-rC CPG (600 A, 72 µmol/g, 123 µmol) were used to assemble 5'NH$_2$-NOX-A12 (2 prePEG) with 2.5 eq. of amidite per nucleotide coupling cycle. Yield after UF: 23985 OD, Purity: 52%, Mass: 14656 Da (found), 14656 Da (calc.).

EXAMPLE 4

PEGylation of 5'NH$_2$-NOX-E36 Using PyBOP for Activation and DMF as Co-Solvent To a solution of 1000 OD (40 mg, 1.54 µmol) of 5'NH$_2$-NOX-E36 (1 prePEG) in 1 mL water was added a solution of 193 mg (600 µmol) Bu$_4$NBr in 750 mL DMF followed by 69 µL (52 mg, 405 µmol) of DIPEA. In another reaction vessel 92 mg (2.31 µmol) of 40 kDa PEG-COOH (JenKem Technology, Allen, Tex., USA) were dissolved in 2.5 mL of DMF. To the PEG solution were added 1.8 mg (3.5 µmol) PyBOP in 60 µL DMF followed by 6.0 µL (4.6 mg, 35 µmol) DIPEA. The PEG solution was then thoroughly vortexed and added to the oligonucleotide solution after 2 minutes. The reaction mixture was gently agitated for 30 minutes. Monitoring of the reaction by RP-HPLC showed 52% conversion.

EXAMPLE 5

PEGylation of 5'NH$_2$-NOX-E36 Using PyBOP for Activation and DMSO as Co-Solvent To a solution of 1000 OD (40 mg, 1.54 µmol) of 5'NH$_2$-NOX-E36 (1 prePEG) in 1 mL of water was added a solution of 193 mg (600 µmol) Bu$_4$NBr in 2 mL DMSO followed by 69 µL (52 mg, 405 µmol) of DIPEA. In another reaction vessel 92 mg (2.31 µmol) of 40 kDa PEG-COOH (JenKem Technology, Allen, Tex., USA) were dissolved in 0.5 mL of ACN. To the PEG solution were added 1.8 mg (3.5 µmol) PyBOP in 60 µL ACN followed by 6.0 µL (4.6 mg, 35 µmol) DIPEA. The PEG solution was then thoroughly vortexed and added to the oligonucleotide solution after 2 minutes. The reaction mixture was gently agitated for 30 minutes. Monitoring of the reaction by RP-HPLC showed 60% conversion.

EXAMPLE 6

PEGylation of 5'NH$_2$-NOX-E36 Using TBTU for Activation

To a solution of 1000 OD (40 mg, 1.54) 5'NH$_2$-NOX-E36 (1 prePEG) in 1 mL of water was added a solution of 193 mg (600 µmol) Bu$_4$NBr in 2 mL DMSO followed by 69 µL (52 mg, 405 µmol) of DIPEA. In another reaction vessel 92 mg (2.31 µmol) of 40 kDa PEG-COOH (JenKem Technology, Allen, Tex., USA) were dissolved in 0.5 mL of ACN. To the PEG solution were added 1.1 mg (3.5 µmol) TBTU in 60 µL ACN followed by 6.0 µL (4.6 mg, 35 µmol) DIPEA. The PEG solution was then thoroughly vortexed and added to the oligonucleotide solution after 2 minutes. The reaction mixture was gently agitated for 30 minutes. Monitoring of the reaction by RP-HPLC showed 59% conversion.

EXAMPLE 7

PEGylation of 5'NH$_2$-NOX-E36 Using COMU for Activation

To a solution of 1000 OD (40 mg, 1.54 µmol) 5'NH$_2$-NOX-E36 (1 prePEG) in 1 mL of water was added a solution of 193 mg (600 µmol) Bu$_4$NBr in 2 mL DMSO followed by 69 µL (52 mg, 405 µmol) DIPEA. In another reaction vessel 92 mg (2.31 µmol) of 40 kDa PEG-COOH (JenKem Technology, Allen, Tex., USA) were dissolved in 0.5 mL of ACN. To the PEG solution were added 1.5 mg (3.5 µmol) COMU in 60 µL ACN followed by 6.0 µL (4.6 mg, 35 µmol) DIPEA. The PEG solution was then thoroughly vortexed for 2 minutes and added to oligonucleotide solution. The reaction mixture was gently agitated for 30 minutes. Monitoring of the reaction by RP-HPLC showed 45% conversion.

EXAMPLE 8

PEGylation of 5'NH$_2$-NOX-E36 in the Presence of Bu$_4$NBr Using HBTU for Activation To a solution of 1000 OD (40 mg, 1.54 µmol) 5'NH$_2$-NOX-E36 (1 prePEG) in 1 mL of water was added a solution of 193 mg (600 µmol) Bu$_4$NBr in 2 mL DMSO followed by 69 µL (52 mg, 405 µmol) DIPEA. In another reaction vessel 92 mg (2.31 µmol) of 40 kDa PEG-COOH (JenKem Technology, Allen, Tex., USA) were dissolved in 0.5 mL of ACN. To the PEG solution were added 1.3 mg (3.5 µmol) HBTU in 7.5 µL ACN followed by 6.0 µL (4.6 mg, 35 µmol) DIPEA. The PEG solution was then thoroughly vortexed for 5 minutes and added to the oligonucleotide solution. The reaction mixture was gently agitated for 30 minutes. Monitoring of the reaction by RP-HPLC showed 42% conversion.

EXAMPLE 9

PEGylation of 5'NH$_2$-NOX-E36 Without Bu$_4$NBr Using HBTU for Activation

To a solution of 6000 OD (240 mg, 9.23 µmol) 5'NH$_2$-NOX-E36 (1 prePEG) in 6 mL of water were added 12 mL of DMSO followed by 414 µL (307 mg, 2.38 mmol) of DIPEA. In another reaction vessel 554 mg (13.8 µmol) of 40 kDa PEG-COOH (JenKem Technology, Allen, Tex., USA) were dissolved in 2.5 mL of ACN. To the PEG solution were added 7.85 mg (20.7 µmol) HBTU in 100 µL ACN followed by 36.0 µL (26.8 mg, 207 µmol) DIPEA. The PEG solution was then thoroughly vortexed for 5 minutes and added to the oligonucleotide solution. The reaction mixture was gently agitated for 30 minutes. Monitoring of the reaction by RP-HPLC showed 45.5% conversion.

EXAMPLE 10

PEGylation of 5'NH$_2$-NOX-A12 Without Bu$_4$NBr Using HBTU for Activation

To a solution of 15966 OD (638 mg, 19.6 µmol, 50% FLP) 5'NH$_2$-NOX-A12 (2 prePEG) in 16 mL of water were added 32 mL of DMSO followed by 1.12 mL of DIPEA. In another reaction vessel 1.97 g (49.3 µmol) of 40 kDa PEG-COOH (JenKem Technology, Allen, Tex., USA) were dissolved in 8 mL of ACN. To the PEG solution were added 19.9 mg (52.5 µmol) HBTU in 200 µL of ACN followed by 83 µL of DIPEA. The PEG solution was then thoroughly vortexed for 5 minutes and added to the oligonucleotide solution. The reaction mixture was gently agitated for 30 minutes. Monitoring of the reaction by RP-HPLC showed 58% conversion.

EXAMPLE 11

Biotinylation of 5'NH$_2$-NOX-A12 Using HBTU for Activation

To a solution of 200 OD (8 mg, 0.237 µmol, 50% FLP) 5'NH$_2$-NOX-A12 (2 prePEG) in 200 µL of water were added 400 µL of DMSO followed by 12.5 mL of DIPEA. In another reaction vessel 0.167 mg (0.683 µmol) of biotin were dissolved in 90 µL of DMSO. To the biotin solution were added 0.259 mg (0.683 µmol) HBTU in 10 µL of ACN followed by 1.8 µL of DIPEA. The biotin solution was then thoroughly vortexed for 1 minute and added to the oligonucleotide solution. The reaction mixture was gently agitated for 30 minutes. Monitoring of the reaction by RP-HPLC showed 55% conversion. The crude product was precipitated by addition of 20 µL of 3 M sodium acetate solution and 10 mL of EtOH and stored at −20° C. for 2 h. The precipitate was collected by centrifugation (4000 g) and decantation. The pellet was dissolved in water and desalted by size exclusion chromatography to yield 159 OD (6.4 mg, 0.192 µmol) of biotinylated NOX-A12 with 45% purity by IEX-HPLC, MS: 14883 Da (calc.), 14883 Da (found).

EXAMPLE 12

UF-Recycling of Excess 40 kDa PEG-COOH After Pegylation of 5'NH$_2$-NOX-A12

An aliquot of 7983 OD of the crude NOX-A12 PEGylation product prepared according to example 10 was subjected to tangential-flow ultrafiltration (UF) using a 30 kDa molecular weight cut off (MWCO) regenerated cellulose membrane (Sartorius, Göttingen, D). The pump pressure was set to 1 bar and 10 L of water were used as feed. The retentate was harvested and freeze dried to yield 0.87 g (7264 OD) of a colorless solid. The filtrate subsequently was concentrated and desalted by tangential-flow filtration using a 2 kDa cut off regenerated cellulose membrane (Sartorius, Göttingen, D). The pump pressure was set to 1 bar and water was used as feed. The method was continued until the filtrate showed a conductivity of less than 20 µS/cm. The retentate was harvested and freeze dried to yield 0.51 g of 40 kDa PEG-COOH as colorless solid.

EXAMPLE 13

Ultrafiltration of the Crude NOX-A12 PEGylation Mixture

Another aliquot of 7983 OD of the crude NOX-A12 PEGylation product prepared according to example 10 was subjected to tangential-flow ultrafiltration (UF) using a 2 kDa MWCO regenerated cellulose membrane (Sartorius, Göttingen, D). The pump pressure was set to 1 bar and 10 L of water were used as feed. The retentate was harvested and freeze dried to yield 1.38 g (7829 OD) of a colorless solid.

EXAMPLE 14

IEX-HPLC Purification and Subsequent UF of PEGylated NOX-A12

The crude NOX-A12 product of 0.87 g (7264 OD) obtained in example 12 was further purified by IEX-HPLC chromatography. An aqueous solution of a 6000 OD sample was charged on a 12 mL TOSOH Super Q5PW IEX-HPLC column (500 OD/mL resin, 50° C.) and eluted at 50° C. by applying a gradient of the following buffer system (buffer A: 25 mM Na2HPO4, pH 7.5, 10% ACN; buffer B: 25 mM $Na_2HPO_4$, 1 M NaBr, pH 7.5, 10% ACN; gradient: 5% B to 35% B in 25CV). All product containing fractions (>75% FLP by IEX-HPLC) were combined (842 OD), desalted by UF using a 5 kDa MWCO regenerated cellulose membrane (Millipore, Bedford, Mass.) and finally freeze dried. Yield: 801 OD, 76% FLP.

EXAMPLE 15

IEX-HPLC-Recycling of Excess 40 kDa PEG-COOH After PEGylation of 5'$NH_2$-NOX-A12

The crude NOX-A12 product (1.38 g, 7829 OD) obtained in example 13 was further purified by IEX-HPLC chromatography. An aqueous solution of a 6000 OD sample was charged on a 12 mL TOSOH Super Q5PW IEX-HPLC column (500 OD/mL resin, 50° C.) and eluted at 50° C. by applying a gradient of the following buffer system (buffer A: 25 mM $Na_2HPO_4$, pH 7.5, 10% ACN; buffer B: 25 mM $Na_2HPO_4$, 1 M NaBr, pH 7.5, 10% ACN; gradient: 5% B to 35% B in 25CV). During loading and 2CV post load wash the flow-through was collected, desalted by 2 kDa MWCO regenerated cellulose membrane (Sartorius, Göttingen, D) and freeze dried to yield 410 mg of a colorless solid of 40 kDa PEG-COOH. All product containing fractions (>75% FLP by IEX-HPLC) were combined (1004 OD), desalted by UF using a 5 kDa MWCO regenerated cellulose membrane (Millipore, Bedford, MA) and finally freeze dried. Yield: 1042 OD, 76% FLP.

EXAMPLE 16

Drying of Recycled 40 kDa PEG-COOH for Subsequent Use in the PEGylation of 5'$NH_2$-NOX-A12

40 kDa PEG-COOH recovered by IEX-HPLC chromatography or tangential flow filtration as exemplified in examples 12 and 15 was dissolved in acetonitrile (20 mL/g) and stored over molecular sieve drying pads overnight to remove any residual water. The molecular sieve was removed and the PEG solution was concentrated under reduced pressure.

EXAMPLE 17

PEGylation of 5'$NH_2$-NOX-A12 Using "Fresh" 40 kDa PEG-COOH and HBTU for Activation To a solution of 100 OD (4 mg, 0.14 µmol, 50% FLP) 5'$NH_2$-NOX-A12 (2 prePEG) in 100 µL of water were added 200 µL of DMSO followed by 7.5 mL of DIPEA. In another reaction vessel 13.7 mg (0.34 µmol) of "fresh" 40 kDa PEG-COOH (JenKem Technology, Allen, Tex., USA) were dissolved in 60 µL of ACN. To the PEG-COOH solution were added 0.13 mg (0.34 µmol) HBTU in 10 µL ACN followed by 0.6 µL of DIPEA. The PEG solution was thoroughly vortexed for 5 minutes and added to the oligo-nucleotide solution. The reaction mixture was gently agitated for 30 minutes. Monitoring of the reaction by RP-HPLC showed 43% conversion.

EXAMPLE 18

PEGylation of 5'$NH_2$-NOX-A12 Using "UF-Recovered" 40 kDa PEG-COOH and HBTU for Activation To a solution of 100 OD (4 mg, 0.14 µmol, 50% FLP) 5'$NH_2$-NOX-A12 (2 prePEG) in 100 µL of water were added 200 µL of DMSO followed by 7.5 mL of DIPEA. In another reaction vessel 13.7 mg (0.34 µmol) of "UF-recovered" and dried (obtained as in example 12 and 16) 40 kDa PEG-COOH were dissolved in 60 µL of ACN. To the PEG solution were added 0.13 mg (0.340 µmol) HBTU in 10 µL of ACN followed by 0.6 µL DIPEA. The PEG-COOH solution was thoroughly vortexed for 5 minutes and added to the oligonucleotide solution. The reaction mixture was gently agitated for 30 minutes. Monitoring of the reaction by RP-HPLC showed 48% conversion.

EXAMPLE 19

PEGylation of 5'$NH_2$-NOX-A12 Using "IEX-HPLC Recovered" 40 kDa PEG-COOH and HBTU for Activation To a solution of 100 OD (4 mg, 0.14 µmol, 50% FLP) 5'$NH_2$-NOX-A12 (2 prePEG) in 100 µL of water were added 200 µL of DMSO followed by 7.5 mL of DIPEA. In another reaction vessel 13.7 mg (0.34 µmol) of "IEX-HPLC recovered" and dried (obtained as in examples 15 and 16) 40 kDa PEG-COOH were dissolved in 60 µL of ACN. To the PEG solution were added 0.13 mg (0.34 µmol) HBTU in 10 µL of ACN followed by 0.6 µL of DIPEA. The PEG-COOH solution was thoroughly vortexed for 5 minutes and added to the oligonucleotide solution. The reaction mixture was gently agitated for 30 minutes. Monitoring of the reaction by RP-HPLC showed 47% conversion.

EXAMPLE 20

Solid-Phase Synthesis of 5'$NH_2$-NOX-A12

Applying the procedure described in Example 1, 1.70 g of L-rC CPG (600 Å, 72 µmol/g, 122 µmol) were used to assemble 5'$NH_2$-NOX-A12 (2 prePEG) with 2.5 eq. of amidite per nucleotide coupling cycle. Yield after deprotection and UF: 23378 OD, Purity: 49%, Mass: 14656 Da (found), 14656 Da (calc.).

EXAMPLE 21

PEGylation of 5'$NH_2$-NOX-A12 with "Fresh" 40 kDa PEG-COOH and Subsequent Down-Stream Processing to Produce NOX-A12

To a solution of 6000 OD (240 mg, 7.86 µmol, 48% FLP) 5'$NH_2$-NOX-A12 (2 prePEG, synthesized according to example 20 in 6 mL of water were added 12 mL of DMSO followed by 0.42 mL of DIPEA. In another reaction vessel 628 mg (15.7 µmol) of 40 kDa PEG-COOH (JenKem Technology, Allen, Tex., USA) were dissolved in 2.55 mL of ACN. To the PEG solution were added 5.96 mg (15.7 µmol) HBTU in 50 µL of ACN followed by 40 µL of DIPEA. The PEG solution was thoroughly vortexed for 5 minutes and added to the oligonucleotide solution. The reaction mixture was gently agitated for 30 minutes. Monitoring of the reaction by RP-HPLC showed 39% conversion. An additional aliquot of 0.5eq of PEG-COOH was prepared by dissolving 157 mg (1.97 µmol) of 40 kDa PEG-COOH (JenKem Technology, Allen, Tex., USA) in 0.7 mL of ACN. To the PEG solution were added 1.49 mg (1.97 µmol) HBTU in 12.5 µL of ACN followed by 10 µL of DIPEA. The PEG solution was thoroughly vortexed for 5 minutes and added to oligonucleotide solution. The reaction mixture was gently agitated for 30 minutes. The renewed monitoring of the reaction by RP-HPLC showed 52% conversion. Another addition of 0.5 eq of activated PEG-COOH led to 58% conversion after additional 30 minutes. The reaction was stopped by dilution into 500 mL water and subjected to tangential-flow filtration using a 30 kDa MWCO regenerated cellulose membrane (Sartorius, Göttingen, D). The pump pressure was set to 1 bar and 20 L of water were used as feed. The retentate was harvested to yield 5581 OD. The crude NOX-A12 product was further purified by IEX-HPLC chromatography. The product was charged on a 12 mL TOSOH Super Q5PW IEX-HPLC column (500 OD/mL resin, 50° C.) and eluted at 50° C. by applying a gradient of the following buffer system (buffer A: 25 mM Tris, pH 7.5, 10% ACN; buffer B: 25 mM Tris, 2 M NaCl, pH 7.5, 10% ACN; gradient: 5% B to 35% B in 25CV). All product containing fractions (>75% FLP by IEX-HPLC) were combined, desalted by UF using a 2 kDa MWCO regenerated cellulose membrane (Millipore, Bedford, Mass.) and finally freeze dried. Yield: 1474 OD, 75 FLP.

EXAMPLE 22

PEGylation of 5'NH$_2$-NOX-A12 with "IEX-HPLC Recovered" 40 kDa PEG-COOH and Subsequent Down-Stream Processing to Produce NOX-A12

To a solution of 6000 OD (240 mg, 7.86 µmol, 48% FLP) 5'NH$_2$-NOX-A12 (2 prePEG, synthesized according to example 20) in 6 mL of water, 12 mL of DMSO followed by 0.42 mL of DIPEA were added. In another reaction vessel 628 mg (15.7 µmol) of "IEX-HPLC recovered" and dried 40 kDa PEG-COOH (obtained as in examples 15 and 16) were dissolved in 2.55 mL of ACN. To the PEG solution were added 5.96 mg (15.7 µmol) HBTU in 50 µL of ACN followed by 40 µL of DIPEA. The PEG solution was thoroughly vortexed for 5 minutes before it was added to the oligonucleotide solution. The reaction mixture was gently agitated for 30 minutes. Monitoring of the reaction by RP-HPLC showed 29% conversion. An additional aliquot of 0.5 eq. of PEG-COOH was prepared by dissolving 157 mg (1.97 µmol) of "IEX-recovered" and dried 40 kDa PEG-COOH in 0.7 mL of ACN. To the PEG solution were added 1.49 mg (1.97 µmol) HBTU in 12.5 µL of ACN followed by 10 µL of DIPEA. The PEG solution was thoroughly vortexed for 5 minutes and added to the oligonucleotide solution. The reaction mixture was gently agitated for 30 minutes. The renewed monitoring of the reaction by RP-HPLC showed 37% conversion. A second and third 0.5 eq. addition of activated "IEX-recovered" and dried PEG-COOH led to 45% and 52% conversion after additional 30 minutes. The reaction was stopped by dilution into 500 mL of water and subjected to tangential-flow filtration using a 30 kDa MWCO regenerated cellulose membrane (Sartorius, Göttingen, D). The pump pressure was set to 1 bar and 20 L of water were used as feed. The retentate was harvested and freeze dried to yield 5711 OD. The crude NOX-A12 product was further purified by IEX-HPLC chromatography. The product was charged on a 12 mL TOSOH Super Q5PW IEX-HPLC column (500 OD/mL resin, 50° C.) and eluted at 50° C. by applying a gradient of the following buffer system (buffer A: 25 mM Tris, pH 7.5, 10% ACN; buffer B: 25 mM Tris, 2 M NaCl, pH 7.5, 10% ACN; gradient: 5% B to 35% B in 25CV). All product containing fractions (>75% FLP by IEX-HPLC) were combined, desalted by UF using a 2 kDa MWCO regenerated cellulose membrane (Millipore, Bedford, Mass.) and finally freeze dried. Yield: 1242 OD, 70% FLP.

The features of the present invention disclosed in the specification, the claims and/or the drawings may both separately and in any combination thereof be material for realizing the invention in various forms thereof.

The invention claimed is:

1. A method for the preparation of a modified nucleic acid molecule comprising a nucleic acid moiety and a non-nucleic acid moiety by reacting a first reactant and a second reactant, wherein the first reactant comprises the non-nucleic acid moiety and a carboxyl group, wherein said non-nucleic acid moiety comprises a polyalkoxy compound and wherein the second reactant comprises an amino-modified nucleic acid molecule comprising the nucleic acid moiety and an amino modification comprising an amino group which is attached to the nucleic acid moiety, wherein the method comprises the following steps:
 a) activating the carboxyl group of the first reactant by a condensation reagent in a water miscible organic solvent, and
 b) reacting the activated carboxyl group of step a) and the amino group of the amino modification of the amino-modified nucleic acid molecule of the second reactant, dissolved in water or in a mixture of a water miscible organic solvent and water,
 wherein the modified nucleic acid molecule is formed.

2. The method of claim 1, wherein the amino-modified nucleic acid molecule is dissolved in a mixture of water and a water miscible organic solvent in the presence of a quaternary ammonium salt and/or, wherein the activated first reactant of step a) is added to the amino-modified nucleic acid molecule dissolved in water or in a mixture of a water miscible organic solvent and water.

3. The method of claim 1, wherein
 the amino-modified nucleic acid molecule comprises amino-modified aptamers, amino-modified Spiegelmers, amino-modified immunostimulatory nucleic acids, amino-modified siRNA, amino-modified miRNA molecules and/or amino-modified nucleic acid antisense molecules, and/or
 the nucleic acid moiety comprises aptamers, Spiegelmers, immunostimulatory nucleic acids, siRNA's, miRNA molecules and nucleic acid antisense molecules.

4. The method of claim 1, wherein in step b), an excess of molecules of the activated first reactant over the amino-modified nucleic acid molecules is used.

5. The method of claim 4, wherein the excess is expressed as a molar ratio of molecules of the activated first reactant and the amino-modified nucleic acid molecules, wherein the molar ratio is from about 1.1 to about 10.

6. The method of claim 1, wherein for activating the first reactant according to step a), the first reactant is dissolved in a water miscible organic solvent, and a condensing agent, and subsequently a base is added thereto.

7. The method of claim 6, wherein the base is a non-nucleophilic base selected from the group consisting of diisopropylethylamine (DIPEA), trimethylamine and DBU.

8. The method of claim 6, wherein the condensing agent is selected from the group consisting of a phosphonium salt, a uronium salt and a carbodiimide.

9. The method according to claim 8,
 wherein the phosphonium salt is selected from the group consisting of BOP, PyBOP, PyBrop, AOP, PyAOP, BrOP and PyClOP;
 the uronium salt is selected from the group consisting of HCTU, TCTU, TBTU, HBTU, HATU, TOTU and COMU; and
 the carbodiimide is selected from the group consisting of DCC (N,N'-dicyclohexylcarbodiimide), EDC (1-ethyl-3-(3-dimethylaminopropyl)carbodiimide) and DIC (N,N'-diisopropylcarbodiimide).

10. The method of claim 1, wherein the water miscible organic solvent is selected from the group consisting of methanol, ethanol, n-propanol, isopropanol, n-butanol, sec-butanol, tert-butanol, dimethyl sulfoxide, diethyl sulfoxide, methyl ethyl sulfoxide, formamide, methyl formamide, dimethyl formamide, ethyl formamide, ethyl methyl formamide, diethyl formamide, 2-pyrrolidone, N-methyl pyrrolidone, N-ethylpyrrolidone, acetonitrile, acetone, ethyl methyl ketone, methyl propyl ketone, diethyl ketone, methyl isopropyl ketone, methyl formate, ethyl formate, propyl formate, isopropyl formate, methyl acetate, ethyl acetate, methyl propanoate, tetrahydrofuran and dioxan.

11. The method of claim 6, wherein a molar ratio of the base to the first reactant is equal to or greater than 1.

12. The method of claim 1, wherein in step b), the activated first reactant of step a) is added to the amino-modified nucleic acid molecules until 80% to 100% or 90% to 100% of the amino-modified molecules are reacted with the first reactant.

13. The method of claim 1, wherein after completion of step b), any non-reacted first reactant is separated by ultrafiltration and/or chromatography.

14. The method of claim 13, wherein the separated first reactant is recycled and used in step a).

15. The method of claim 1, wherein the polyalkoxy compound is a straight or a branched polyalkoxy compound.

16. The method of claim 1, wherein the polyalkoxy compound is selected from the group consisting of polyethylene glycol, polypropylene glycol, poly butylene glycol and polyglycerol.

17. The method of claim 1, wherein the polyalkoxy compound is polyethylene glycol.

18. The method of claim 1, wherein the polyalkoxy compound comprises a molecular weight of 5,000 Da to 100,000 Da, 20,000 Da to 80,000 or 40,000 Da.

19. A modified nucleic acid molecule obtained by the method of claim 1.

20. The method of claim 1, wherein said nucleic acid moiety comprises an aptamer comprising L-nucleotides and/or D-nucleotides.

21. The method of claim 6, wherein said base comprises DIPEA.

22. The method of claim 1, wherein said water miscible organic solvent comprises dimethyl formamide, acetonitrile or dimethyl sulfoxide.

23. The method of claim 1, wherein after completion of step b), any non-reacted first reactant is separated by ion exchange chromatography.

* * * * *

SEQUENCE LISTING

<160> NUMBER OF SEQ ID NOS: 2

<210> SEQ ID NO 1
<211> LENGTH: 40
<212> TYPE: RNA
<213> ORGANISM: artifical
<220> FEATURE:
<221> NAME/KEY: misc_feature
<223> OTHER INFORMATION: synthetic
<220> FEATURE:
<221> NAME/KEY: misc_feature
<222> LOCATION: (1)..(40)
<223> OTHER INFORMATION: nucleotides are L-nucleotides

<400> SEQUENCE: 1
gcacgucccu caccggugca agugaagccg uggcucugcg            40

<210> SEQ ID NO 2
<211> LENGTH: 45
<212> TYPE: RNA
<213> ORGANISM: artifical
<220> FEATURE:
<221> NAME/KEY: misc_feature
<223> OTHER INFORMATION: synthetic
<220> FEATURE:

```
<221> NAME/KEY: misc_feature
<222> LOCATION: (1)..(45)
<223> OTHER INFORMATION: nucleotides are L-nucleotides

<400> SEQUENCE: 2
gcguggugug aucuagaugu auuggcugau ccuagucagg uacgc            45
```